(12) United States Patent
Sexton et al.

(10) Patent No.: US 11,083,954 B2
(45) Date of Patent: Aug. 10, 2021

(54) METHOD AND SYSTEM FOR CONTESTING AND DETERMINING THE VICTOR OF A COMBAT SPORT

(71) Applicant: 2020 Armor Inc., North York (CA)

(72) Inventors: William Kyle Sexton, Norman, OK (US); Austin Thomas Jones, Norman, OK (US); Ali Ghafour, North York (CA); Michael Todd Sexton, Norman, OK (US)

(73) Assignee: 2020 Armor, Inc., Ontario (CA)

( * ) Notice: Subject to any disclaimer, the term of this patent is extended or adjusted under 35 U.S.C. 154(b) by 0 days.

(21) Appl. No.: 16/751,924

(22) Filed: Jan. 24, 2020

(65) Prior Publication Data

US 2020/0155916 A1    May 21, 2020

Related U.S. Application Data

(63) Continuation of application No. 16/030,372, filed on Jul. 9, 2018, now Pat. No. 10,688,373, which is a
(Continued)

(51) Int. Cl.
*A63B 71/06* (2006.01)
*A63B 71/12* (2006.01)
(Continued)

(52) U.S. Cl.
CPC .......... *A63B 71/06* (2013.01); *A41D 13/0518* (2013.01); *A61B 5/1112* (2013.01);
(Continued)

(58) Field of Classification Search
USPC .......................................................... 700/92
See application file for complete search history.

(56) References Cited

U.S. PATENT DOCUMENTS

| 4,580,296 A | 4/1986 | Cano |
| 5,199,705 A | 4/1993 | Jenkins et al. |

(Continued)

FOREIGN PATENT DOCUMENTS

| CN | 101376056 | 3/2009 |
| CN | 103623560 | 3/2014 |

(Continued)

OTHER PUBLICATIONS

English Abstract of CN205494914.
(Continued)

*Primary Examiner* — Pierre E Elisca
(74) *Attorney, Agent, or Firm* — Robert S. Silver; Langer, Grogan & Diver, P.C.

(57) ABSTRACT

A data collection and display system for use in a combat sport including:
i. A trunk protector for a combat sport participant, the trunk protector including:
a. protective padding,
b. at least one impact sensor,
c. at least one microprocessor integral with the protective padding, for collecting and analyzing data from the at least one impact sensor,
d. at least one display area, integral with the trunk protector, for displaying information related to the combat sport and combat sport participant; and an energy based method for scoring combat sports.

6 Claims, 19 Drawing Sheets

Related U.S. Application Data continuation-in-part of application No. PCT/CA2017/050025, filed on Jan. 10, 2017.

(60) Provisional application No. 62/277,173, filed on Jan. 11, 2016.

(51) Int. Cl.
  *A63B 69/00* (2006.01)
  *A61B 5/11* (2006.01)
  *A61B 5/00* (2006.01)
  *A41D 13/05* (2006.01)

(52) U.S. Cl.
  CPC ........... *A61B 5/1118* (2013.01); *A61B 5/1121* (2013.01); *A61B 5/6803* (2013.01); *A61B 5/6804* (2013.01); *A63B 69/004* (2013.01); *A63B 71/0622* (2013.01); *A63B 71/12* (2013.01); *A61B 2503/10* (2013.01); *A61B 2562/0219* (2013.01); *A61B 2562/0247* (2013.01); *A63B 2071/065* (2013.01); *A63B 2071/0647* (2013.01); *A63B 2209/08* (2013.01); *A63B 2220/10* (2013.01); *A63B 2220/12* (2013.01); *A63B 2220/16* (2013.01); *A63B 2220/30* (2013.01); *A63B 2220/40* (2013.01); *A63B 2220/53* (2013.01); *A63B 2220/803* (2013.01); *A63B 2225/50* (2013.01); *A63B 2225/54* (2013.01); *A63B 2244/10* (2013.01); *A63B 2244/102* (2013.01); *A63B 2244/106* (2013.01)

(56) References Cited

U.S. PATENT DOCUMENTS

| | | | |
|---|---|---|---|
| 6,183,365 | B1 | 2/2001 | Tonomura et al. |
| 7,552,031 | B2 | 6/2009 | Vock et al. |
| 7,891,231 | B2 | 2/2011 | Song |
| 8,021,281 | B2 | 9/2011 | Forsell et al. |
| 8,485,879 | B2 | 7/2013 | Lin et al. |
| 8,984,954 | B2 | 3/2015 | Merrell et al. |
| 9,208,692 | B2 * | 12/2015 | Considine ................ G09B 5/00 |
| 9,227,128 | B1 | 1/2016 | Carfagna, Jr. |
| 2006/0047447 | A1 | 3/2006 | Brady et al. |
| 2007/0281125 | A1 | 12/2007 | Moore, III et al. |
| 2009/0235761 | A1 | 9/2009 | Song |
| 2012/0088222 | A1 * | 4/2012 | Considine ................ G09B 7/02 434/362 |
| 2012/0214647 | A1 | 8/2012 | Ji et al. |
| 2014/0260653 | A1 | 9/2014 | Merrell et al. |

FOREIGN PATENT DOCUMENTS

| | | |
|---|---|---|
| CN | 204557747 | 8/2015 |
| CN | 205494914 | 8/2016 |
| CN | 205730257 | 11/2016 |
| EP | 0458853 | 4/1991 |
| JP | H08112391 | 5/1996 |
| JP | H09325081 | 12/1997 |
| KR | 20100092733 | 8/2010 |
| KR | 101018038 | 3/2011 |
| KR | 101093669 | 12/2011 |
| KR | 20140066024 | 5/2014 |
| KR | 101446604 | 10/2014 |
| WO | WO2010005169 | 1/2010 |
| WO | WO2011079297 | 6/2011 |

OTHER PUBLICATIONS

English Abstract of CN103623560.
English Abstract of CN205730257.
English Abstract of CN101376056.
English Abstract of KR101446604.
English Abstract of KR101093669.
English Abstract of JPH08112391.
English Abstract of KR20100092733.
English Abstract of CN204557747.
English Abstract of KR20140066024.
English Abstract of KR101018038.
International Search Report for related PCT Application No. PCT/CA2017/050025 dated Mar. 22, 2017.
Supplementary Partial European Search Report for related European Patent Application No. EP17738055.
Street Fighter (game), Wikipedia, retrieved on Mar. 2, 2021 from https://ja.wikipedia.org/wiki/ストリートファイター_(ゲーム) ).
English Abstract of JPH09325081.

* cited by examiner

METHOD AND SYSTEM FOR CONTESTING AND DETERMINING THE VICTOR OF A COMBAT SPORT

This Continuation application claims the benefit under 35 U.S.C. § 120 of application Ser. No. 16/030,372 filed on Jul. 9, 2018 which in turn is a bypass continuation in part application which claims priority under 35 USC § 120 of application PCT/CA2017/050025 filed Jan. 10, 2017, which claims benefit of U.S. Ser. No. 62/277,173 filed Jan. 11, 2016, and all of whose entire disclosures are incorporated by reference in their entireties herein.

FIELD OF THE DISCLOSURE

The present disclosure relates generally to combat sports and more specifically to a method and system for contesting and determining the victor of a combat sport or combat match, creating an intuitive interpretation of the many various combat disciplines, measurement technologies for the application of determining physical values of kinematic properties of combatants and events of a combat sport match, such as energy, velocity, acceleration, location and direction, among others, and using that information to derive the status and score of a combat sport match.

The present disclosure further relates to the use of data of a combat sport player post match to analyze the player's performance and identify areas requiring improvement.

The present disclosure further relates to a method and system for use by a player of a combat sport to train for combat and collect and analyze data of a player training for a combat sport.

BACKGROUND

A combat sport consists of two or more players engaging in a form of controlled combat meant to simulate various aspects of genuine fighting. The format of any combat sport attempts to decide quantitatively the winner of a match by applying positive or negative point values to prescribed events in a combat match, such as a player losing a point when he falls in boxing, or when a player is awarded points for delivering a successful kick to the opponent in taekwondo. The specifics of all scoring schemes are many and vary widely but generally follow the premise that the contestant or combatant or player with the higher score at the end of the allotted time is the winner, unless the match is decided by knockout or disqualification, or some other instant win criterion, such as the scoring of an "Ippon" in judo.

Many combat or martial arts disciplines have specific limiting criteria for what is and is not allowable as a scoring action, as well as what is and is not a scoring zone on an opponent. In combat sports, for example taekwondo, which utilize protective gear (such as body protectors, chest protectors and trunk protectors) to cover vital organs, colored zones of the protective gear, which often denote the designation of the player as a color, also often define valid scoring areas.

Currently, and in recent decades, many of the scoring methods in combat sports have undergone technical upgrades and stylistic changes, designed to make matches fairer by reducing and/or removing human bias, making them more adaptable to various strategies, body types and personal styles of the combatants, and making them more intuitive and exciting for modern audiences. Some small changes have been successful, while most have not, resulting in various combat disciplines looking much the same and possessing many of the same unresolved problems.

Using a point system to determine a winner of a combat sport is still very subjective, and the point value attributed to any action is entirely subjective and at times artificial, having little or no basis in any real world qualities to derive that value. For instance, in taekwondo, a punch currently counts for a 1-point value, while a kick may be attributed a 4-point value. This scoring method does not take into account any other qualities of the attacks, meaning for example that a punch, twice as powerful and damaging than a less effective kick, would still register $\frac{1}{4}^{th}$ the value of the less effective kick. Therefore, athletes (combatants and players of combat sports) are often encouraged by the current scoring methods to use less effective or inappropriate combative techniques, which usually incur more points, whether or not it is an intended aspect of the scoring method. This is a flawed facet of scoring which no present method or system has successfully overcome. Prior publications that have attempted to correct some facets of the issues presented here, include those described in U.S. Pat. No. 7,891,231 B2, EP 0458853 B1, WO2010005169A1, U.S. Pat. No. 8,021, 281 B2.

There is a need for a scoring method for combat sports that takes into account the power of a technique when assessing a scoring value.

Nearly all combat disciplines feature an inherent bias toward a prescribed style, despite the full breadth of strategy and personal choice technically allowable under their rules. For instance, while it is fully legal in a taekwondo match to punch the opponent in the torso, the rate of successfully scoring with a punch has been dismally low compared to the rate of successfully scoring with a kick when judged by humans, due to the unique emphasis placed on kicking in taekwondo instruction. Existing scoring solutions, however, have failed to take into account the stylistic differences between the "letter" and the "spirit" of the rules by which humans inherently and often subconsciously operate, to the dissatisfaction of spectators, participants, and sport organizers, despite varied levels of success in technical adherence to the formal enumerated rule set. This results in undesirable behavior through the use of unintuitive, unattractive, and often combatively ineffective attack methods to satisfy the technicalities of the scoring criteria, now bereft of human interpretation in their scoring, and create scores of which humans disapprove.

In taekwondo, such attacks are colloquially known as "PSS kicks", named after the "Protective Scoring System" that is tricked into rewarding improper scores. In standard practice in taekwondo, the PSS has now replaced the scoring duty of human judges, and as such, there exists no person with the authority to undo, compensate for, or prevent the inaccuracies of the rigidly interpreted scoring.

There is a need for a method of determining if an action performed in the course of the match is appropriate of a prescribed style, and/or to adjust the value of any action to align with the human interpretation of a combat sport rule set.

Many martial arts schools suffer from low student enrollment and retention. This may be alleviated by an increased perception of personal student growth through personal statistics. There is a need for an easy to use system that provides data associated with performance of a combat or martial arts player. There is a need for a combat sport scoring system that may operate with or without an external computer, and is reasonably priced.

There is a need for a data collection and display system to reduce subjectivity in scoring methods. There is a need for a body protector for combat sports with an impact sensor and a display area integral with the body protector to display data associated with the combat sport and the combatant.

SUMMARY

The term "chest protector" used herein is synonymous with body protector and/or trunk protector.

The term "combatant" used herein is synonymous with player, opponent and/or contestant.

According to one aspect, there is provided a data collection and display system for use in a combat sport or match, for acquiring, applying, and displaying data relevant to any and all aspects and components of the described subject matter; the display data comprising a first contestant (for example, but not limited to, blue contestant) status indicator for providing at least one of an audience, referee, and contestant or contestants with information pertinent to the contestant designated "first" or "blue", a clock for detailing the time remaining in a current round of a combat match, a second contestant (for example, but not limited to, red contestant) status indicator for providing at least one of an audience, referee and contestant or contestants with information pertinent to the contestant designated "second" or "red", and a protocol of play of the combat sport or match adaptable to specifications of desired parameters. In one instance, each of said first and said second contestants are individuals. In another instance, the first contestant is and individual and the second contestant is a striking item, such as, but not limited to a punching bag, kicking bag or the like.

According to yet another embodiment, there is provided a data collection and display system for use in a combat sport or match, for use with a single user. In another embodiment said system is for use with at least two users.

According to another aspect, there is provided a combat sport including the use of the data collection and display system described herein.

According to yet another aspect, there is provided a method and system of contesting and determining the victor of a combat sport or match and preferably creating an intuitive interpretation of classical combat disciplines.

According to yet another aspect, there is provided a method and system of calculating a value of a scoring action, data collection and display applicable to various combat sports such as, but not limited to, taekwondo, boxing, karate, kickboxing, muay thai, mixed martial arts, and any combination or reconfiguration thereof, and to any style or system of physical combat not yet imagined or defined.

According to yet another aspect, there is provided a method and system of calculating a value of a scoring action, data collection and display for a combat sport that simulates a real-world combative encounter, as is the basis for combat sport in general.

According to yet another aspect, there is provided a method and system that records and judges, in exemplary embodiments quantitatively and without bias, at least one scoring action by a combatant engaged in a combat sport or combat training, by the individual merit of the scoring action through the measurement of various non-sport-specific traits, such as, but not limited to, magnitude, placement, and timing.

According to yet another aspect, there is provided a method and system of affecting the value of a scoring action during a match between at least two combat sport participants, said method and system being based on proximity of at least one distance sensor of at least one combat sport participant in relation to at least one distance sensor of at least another combat sport participant during the execution of a successful strike by one combat sport participant to said at least another combat sport participant.

In one embodiment, said at least one distance sensor being a sensor which allows for the derivation of measurement of distance (wholly or partial distance) between two points (preferably between two opponents). In one embodiment, said distance sensor may use at least one of the following for measurement:

sonar, laser, electromagnetic field or a beam of electromagnetic radiation, capacitive, inductive, Doppler effect, radar, Hall effect, infrared, photocell, sound, light, time of flight, radio frequency signal strength, and combinations thereof which allows for distance determination.

In a further embodiment, said distance measurement may be wholly or partial.

According to yet another aspect, there is provided a data collection and display system for use in a combat sport comprising:

i. A trunk protector (or chest protector or body protector) for a combat sport participant, said trunk protector comprising:

a. Protective padding, b. At least one impact and/or energy sensor, in an exemplary embodiment integral with said protective padding, c. At least one microprocessor, in an exemplary embodiment integral with said protective padding, for collecting and analyzing data from said at least one impact sensor, d. At least one display area, integral with said trunk protector, for displaying information selected from the group consisting of: data collected and analyzed by said at least one microprocessor, participant status, participant score, participant health, match time, match number and combinations thereof, and e. At least one power source, in an alternate embodiment, a rechargeable power source, integral with said trunk protector, for powering at least one of said at least one impact sensor, said at least one microprocessor and said at least one display area.

In an alternative embodiment, said data collection and display system for use in a combat sport further comprises at least one transmitter and receiver for transmitting and receiving data of at least one distance signal source, preferably at least two distance signal sources, preferably wirelessly, to said data collection and display system in relation to measurement of at least one of the following:

i) distance between said at least two distance signal sources;

ii) signal strength between said at least two distance signal sources;

iii) time for a signal (or signal source) to arrive at a distance sensor;

iv) and combinations thereof.

In an exemplary embodiment, said at least one impact and/or energy sensor is said protective padding.

In an exemplary embodiment, said at least one impact and/or energy sensor is distinct from said protective padding.

In an exemplary embodiment, said at least one impact and/or energy sensor is removable from said trunk protector.

In an exemplary embodiment, said at least one display area is removable from said trunk protector.

In an exemplary embodiment, said system further comprises a head protector. Preferably said head protector further comprising protective padding and at least one impact and/or energy sensor. In one embodiment, said at least one impact and/or energy sensor is integral with said protective padding. In another embodiment, said at least one impact and/or energy sensor is said protective padding. In yet another embodiment, said at least one impact and/or energy sensor is distinct from said protective padding.

In an exemplary embodiment, said head protector further comprises a transmitter for communicating externally of said head protector.

In an exemplary embodiment, said head protector transmitter allows for transmitting and receiving data of at least one distance signal source, preferably at least two distance signal sources, preferably wirelessly, to said data collection and display system in relation to measurement of at least one of the following:
v) distance between said at least two distance signal sources;
vi) signal strength between said at least two distance signal sources;
vii) time for a signal (or signal source) to arrive at a distance sensor;
viii) and combinations thereof.

In yet another exemplary embodiment, said system further comprises at least one pair of foot guards, shin guards, hand guards, forearm guards and combinations thereof. In exemplary embodiments, each of said at least one pair of foot guards, shin guards, hand guards and forearm guards further comprise protective padding material and at least one motion sensor. In exemplary embodiments, each of said at least one pair of foot guards, shin guards, hand guards and forearm guards further comprise at least one transmitter for communicating externally of said at least one pair of foot guards, shin guards, hand guards and forearm guards.

In another embodiment, each of said at least one pair of foot guards, shin guards, hand guards and forearm guards further comprise a transmitter for external communication with a central processing hub or the like.

In another embodiment, said transmitter of each of said at least one pair of foot guards, shin guards, hand guards and forearm guards allows for transmitting and receiving data of at least one distance signal source, preferably at least two distance signal sources, preferably wirelessly, to said data collection and display system in relation to measurement of at least one of the following:
ix) distance between said at least two distance signal sources;
x) signal strength between said at least two distance signal sources;
xi) time for a signal (or signal source) to arrive at a distance sensor;
xii) and combinations thereof.

In an exemplary embodiment, said trunk protector further comprises a left arm motion sensor, a right arm motion sensor, a left leg motion sensor and a right leg motion sensor.

In an exemplary embodiment, said system further comprises a control panel integral with said trunk protector, more preferably integral with said display area. Preferably said control panel further comprises at least one control for controlling at least one of power, time, health, game mode and combinations thereof.

In yet another exemplary embodiment, said system further comprises a transmitter for communicating externally of said trunk protector, preferably for communicating to an external device. Preferably said external device is a computer, mobile device, the cloud, a second trunk protector and combinations thereof.

In an exemplary embodiment, said display area is selected from audio display, visual display and combinations thereof.

In an exemplary embodiment, said system is for use in contesting and determining a victor of a combat sport.

In an exemplary embodiment, said system is for use in assessing performance of a combat sport participant during a training session.

In an exemplary embodiment, said system further comprises a sensor for quantifying participant information, in one embodiment, selected from the group consisting of body movement, limb movement, angular position, rectilinear position, velocity, acceleration and combinations thereof. In one embodiment, said sensor is selected from the group consisting of an accelerometer, a gyroscope, a compass, a GPS tracker, strain, strain rate and combinations thereof.

In an exemplary embodiment, said participant information is derived from at least one participant hand, at least one participant foot, a participant head, at least one participant elbow, at least one participant knee and combinations thereof.

In an exemplary embodiment, said protective padding is lightweight and able to absorb and/or disperse impact forces typical of combat sports, to reduce injury to a combatant receiving a strike from another combatant.

In one exemplary embodiment, said protective padding is selected from the group consisting of foam, EVA foam, impact-absorbing foam, viscoelastic foam, viscoelastic polyurethane and combinations thereof.

In another exemplary embodiment, said protective padding is Poron XRD™.

In yet another exemplary embodiment, said protective padding and said at least one impact sensor is XOnano Smartfoam™.

In an exemplary embodiment, said at least one impact and/or energy sensor is encased in a housing able to withstand multiple impacts, preferably up to 600,000 impacts of at least about 9000 N of force each.

In yet another exemplary embodiment, said at least one impact and/or energy sensor is able to sense an impact from about 50 N of force to about 9000 N of force.

In yet another exemplary embodiment, said at least one impact and/or energy sensor is able to sense a "trembling shock" impact or significant impact as understood by a person of ordinary skill in the art, typically in Olympic-style taekwondo.

According to yet another embodiment there is provided the use of a data collection and display system, e.g., data collection, analysis and display, described herein in a combat sport. In another embodiment, said data collection, analysis and display generates post combat sport match statistics of a player and a match. In one embodiment, said use is in at least one training session. In another embodiment, said use is in at least one combat sport round or match.

According to yet another embodiment, there is provided in the trunk protector or head protector a conduit to transfer a charge (or signal) from the sensor to a point of measurement. In one embodiment, the conduit is a wire mesh. In an exemplary embodiment, the conduit is a film, preferably a metallized film, e.g., a metallized thermoplastic polymer such as polyethylene terephthalate ("PET"). In exemplary embodiments, the PET is coated (covered) with a conductive material. In exemplary embodiments, the conductive material is a metal. In exemplary embodiments, the metal is selected from the group consisting of aluminum, copper and combinations thereof.

According to yet another aspect, there is provided a data collection system for use in a combat sport comprising:

i. A trunk protector (or chest protector or body protector) for a combat sport participant, said trunk protector comprising:
   a. Protective padding selected from viscoelastic foam, viscoelastic polyurethane and combinations thereof;
   b. At least one impact and/or energy sensor integral with said protective padding,
   c. At least one microprocessor, in one embodiment integral with said protective padding, for collecting and analyzing data from said at least one impact and/or energy sensor, and
   e. At least one power source, in an alternate embodiment, a rechargeable power source, integral with said trunk protector, for powering at least one of said at least one impact and/or energy sensor, and said at least one microprocessor.

In an exemplary embodiment, said at least one impact and/or energy sensor is said protective padding.

In another exemplary embodiment, said at least one impact and/or energy sensor is formed by said protective padding.

There have been outlined, some of the features of the described subject matter in order that the detailed description thereof may be better understood, and in order that the present contribution to the art may be better appreciated. There are additional features of the described subject matter that will be described hereinafter. In this respect, before explaining at least one embodiment of the described subject matter in detail, it is to be understood that the described subject matter is not limited in its application to the details of construction or to the arrangements of the components set forth in the following description or illustrated in the drawings. The subject matter described herein is capable of other embodiments and of being practiced and carried out in various ways. Also, it is to be understood that the phraseology and terminology employed herein are for the purpose of the description and should not be regarded as limiting.

Some of the advantages of the system disclosed herein include:
   i) measurement of impact energy is more realistic than the use of current body protector systems that measure force and pressure;
   ii) motion tracking is able to directly detect and corroborate an impact;
   iii) the present system may differentiate from various striking techniques;
   iv) the present system may be able to determine kick and punch speed and geometry statistics. Some existing systems incorporate magnets or RFIDs such that when a hand or foot of a competitor is proximate a sensor, the sensor reads an impact although it may be a glancing blow or a light touch or an illegal strike. Such systems cannot differentiate legal striking techniques from illegal striking techniques;
   v) the present system may reduce subjective discretionary scoring of combat sports by human judges/referees/officials by:
      a) automatically detecting the legality and strength of impacts to a chest protector and/or a head protector;
      b) collecting objective kinematic data allowing unbiased observations of penalties by a player/combatant during a match;
      c) reducing the number of personnel required to facilitate a match and/or a tournament.
   vi) the present system's use of a protective element comprising a foam, EVA foam, impact-absorbing foam, viscoelastic foam, viscoelastic polyurethane and combinations thereof may:
      a) conform better to the body of a combatant wearing the chest protector or head protector;
      b) provide more comfort to the combatant when executing a technique, such as a kick;
      c) provide a level of protection similar to current systems but slimmer and/or thinner;
      d) increase protection of the combatant receiving a strike with impact intensity (more protection from stronger strikes by another combatant but combatant receiving strikes is still able to feel 1 strikes of less intensity);
      e) last longer than EVA standard foam. Polyurethane foam does not creep with fatigue. Creeping may alter impact sensor response over time.
   vii) Triboelectric foam sensor integrates the scoring and protective elements into a single component which may:
      a) reduce cost and complexity of a system;
      b) increase uniformity of sensor coverage reducing "cold" or "hot" spots on a chest protector and/or head protector;
      c) measure impact energy which is a conserved value independent of impact or shape and mass distribution, in contrast with impact force and pressure;
      d) exhibit no preloading effects; (Some existing systems incorporate cables running along a chest protector leaving gaps and at times causing preloading of the cables and sensors when the chest protector is worn by the combatant leading to uneven sensor zones).
   viii) The retention and display of data in and on the chest protectors respectively facilitates training, recreational and competitive play. Some existing units require a separate computer and specialized wireless hardware for each pair of chest protectors and head protectors, increasing cost, complexity and difficulty in usage and improving competition and gameplay.
   ix) The use of distance measuring between fighters allows for the inclusion of style-driven human interpretation criteria beyond the formal ruleset. Existing scoring solutions simply attempt to adhere to the written rules, which do not fully describe the stylistic conditions of a match that humans find satisfying to watch or participate in.
   x) The radio signal analysis between the fighters' modules which yields the said distance measurement can also yield information regarding specific action qualities to further reward, either alone or in combination with data recorded and analyzed with other integrated sensors, such as the presence and degree of physical rotation in an attack, or yield information regarding specific action qualities to penalize, such as unwarranted avoidance of the match or retreat from the field of play (out of bounds.)
   xi) In the practice application, the signal analysis can study the variance in distance between players in a match, and determine if the unit is being worn on a human or placed on a stationary target, such as a heavy bag or impact mannequin, for the purpose of yielding performance information specific to training against a moving or non-moving target, and to reverse the display of animations between units that are not being worn by humans, as is necessary when the person striking the unit is not wearing the paired unit to the unit being struck.

According to yet another embodiment, there is provided a method of determining a victor in a combat sport match comprising at least one round, preferably at least two rounds, forming a match between at least two players using an energy scoring system, said method comprising:

assigning a predetermined health level to each player prior to each round;

assigning a predetermined time period for a length of each round;

commencing the match and allowing the predetermined time period to start;

reducing the health level of the player receiving a qualifying strike from the other player; wherein:

the player with a health level higher than the other player at the end of the round is declared victor of the round; or the player depleting the health level of the other player to zero at any time during the round is declared victor of the round; such that the player with the most round victories is declared the victor of the match.

In an exemplary embodiment, if a player is knocked out or disqualified during any round of a match, the other player is declared the victor of the match.

According to another aspect, there is provided a method of calculating a value of a scoring action, preferably based on impact and/or energy associated with a strike delivered by a combatant in a combat match between at least two opponents (or combatants), preferably a final magnitude value of a scoring action by an opponent in a combat match between at least two opponents, by quantification of non-sport-specific trait variables selected from magnitude, placement, impact intensity and/or energy and timing, and defining mathematical constants as desired, resulting in a formula customized to preference as desired (i.e. specific combat sport or specific combat rules) for promoting, encouraging, and rewarding any interpretation of proper or desirable action behavior by the opponents; said method comprising:

i) determining a proper or desirable combatant action behavior to promote, encourage, and reward for which to customize a scoring formula;

ii) determining an individual raw magnitude of every scoring action $m_i$;

iii) assigning a placement value, determined by a scoring impact zone l on the combatants, to a $P_{l_i}$ constant;

iv) assigning an independent combination bonus multiplier value to $C_1$ constant;

v) assigning a magnitude, inclusive or exclusive of any modifying variable, per preference, of any desired scoring action to $A_1$ constant;

vi) assigning a magnitude, inclusive or exclusive of any modifying variable, per preference, of any desired scoring action to $A_2$ constant;

vii) assigning a time-dependent combination bonus modifier to $C_2$ constant;

viii) determining the amount of time elapsed between any scoring action and a previous scoring action $t_i$;

ix) assigning a value, of a threshold of elapsed time between scoring actions eligible for application of combination scoring augmentation, to $T_n$ constant; and x) evaluating for $M_s$ and attributing to the relevant combatant to affect status of the match or game mode.

The resulting calculating method is defined as follows:

$$M_s = m_i P_{l_i} + C_{1_n}\left(\frac{A_1 + A_2}{2}\right)\left(C_{2_n} - \frac{t_i}{T_n}\right) \Big| 0 < t_i \le T_n$$

| | Definitions |
|---|---|
| $M_s$ | Scoring magnitude of scoring action |
| $m_i$ | Impact intensity of scoring action |
| $P_{l_i}$ | Placement modifier determined by location |
| $A_1$ | Magnitude of any desired scoring action |
| $A_2$ | Magnitude of any desired scoring action |
| $C_{1_n}$ | Independent combination bonus multiplier |
| $C_{2_n}$ | Time-dependent combination bonus modifier |
| $t_i$ | Time elapsed between scoring actions |
| $T_n$ | Timer of scoring actions eligible to be augmented by combination bonus |
| i | Pertaining to the selected scoring action (i − 1 refers to previous action etc.) |
| n | The number of scoring actions while t < T, reset to 0 when t ≥ T. |
| l | Location value attributed to striking zones |

| | | Constants | |
|---|---|---|---|
| Constant | Preferred Value | Preferred Definitions | Range |
| $P_{l_i}$ | See "P Table" | f(l) | Any real finite number |
| $A_1$ | $M_{s_{i-1}}$, $m_i P_{l_i}$, $m_{i-1} P_{l_{i-1}}$ | $f(M_{s_{i-1}})$, $f(m_i, P_{l_i})$, $f(m_{i-1}, P_{l_{i-1}})$ | Any real finite number |
| $A_2$ | $A_1$, $M_{s_{i-1}}$, $m_i P_{l_i}$, $m_{i-1} P_{l_{i-1}}$ | $A_1$, $f(M_{s_{i-1}})$, $f(m_i, P_{l_i})$, $f(m_{i-1}, P_{l_{i-1}})$ | Any real finite number |
| $C_{1_n}$ | 1 | f(n) | Any real finite number |
| $C_{2_n}$ | 1 | f(n) | Any real finite number |
| $T_n$ | 1 | Arbitrary | Any positive real number |

| $C_{1_n}$ Table | |
|---|---|
| n | $C_1$ |
| 1 | 0 |
| ... | ... |

| $C_{2_n}$ Table | |
|---|---|
| n | $C_2$ |
| 1 | 1 |
| ... | ... |

| $T_n$ Table | |
|---|---|
| n | T |
| 1 | ... |
| ... | ... |

| $P_{l_i}$ Table | |
|---|---|
| l | P |
| Trunk | ... |
| Head | ... |
| ... | ... |

In an exemplary embodiment, the following substitutions, definitions and simplifications yield a preferred final calculating method of the many various final score calculating method possibilities:

$$M_s = m_i P_{l_i} + C_{1_n}\left(\frac{A_1 + A_2}{2}\right)\left(C_{2_n} - \frac{t_i}{T_n}\right) \Big| 0 < t_i \le T_n$$

Define:

$$C_1 = 1,\ C_2 = 1,\ T_n = 1,\ A_1 = A_2 = m_i P_{l_i},\ P_{l_{Trunk}} = 1,\ P_{l_{Head}} = 2$$

$$M_s = m_i P_{l_i} + \left(\frac{2 m_i P_{l_i}}{2}\right)\left(1 - \frac{t_i}{1}\right)$$

$$M_s = m_i P_{l_i} + m_i P_{l_i}(1 - t_i)$$

In an exemplary embodiment, a calculation to determine the final magnitude of a scoring action is then performed by a computing device using the following method:

$$M_s = m_i P_{l_i} + m_i P_{l_i}(1 - t_i)$$

In this exemplary embodiment, $M_s$ represents the final magnitude of the scoring action, comprised of a single or multiple scoring impacts, $P_{l_i}$ represents the placement modifier (or multiplier) coefficient determined by the scoring impact zone on the opponent, wherein the most preferable embodiment allocates a value of 1 to an impact to the trunk and a value of 2 to an impact to the head, $m_i$ represents the raw magnitude of the impact, and $t_i$ represents elapsed time since the last scoring impact from the respective contestant. The purpose for introducing the variable $t_i$ into this scoring model is to include a consideration for the timing of a scoring impact in relation to other scoring impacts, which is not present in any combat sport, to benefit the contestant who scores consecutively within the 1 second allowed in the $(1-t_i)$ component. Therefore, the lower the $t_i$ value, the higher the combination bonus awarded for that action, relative to that action. Because the variable $t_i$ is technically undefined until the second scoring impact per contestant per round, it will by default in each round be defined as equal to 1 until it can be defined as an independent value. The function of the combination bonus is to objectively, quantitatively, and commensurately reward the behaviors which make the match exciting and intuitive to spectate. The more consecutive scoring impacts performed in combination, and the chronologically closer the scores within the combinations, the more and better combination bonuses a contestant will acquire, thereby rendering a quantitative stylistic advantage to the more intense contestant and discouraging conservative fighting.

According to yet another embodiment, the method of calculating a value of a scoring action, preferably based on impact and/or energy associated with a strike delivered by a combatant in a combat match between at least two opponents (or combatants) further comprises an element which takes into account distance between combatants during execution of a strike component to calculate a value of a scoring action, comprising:

i) determining a proper or desirable combatant action behavior to promote, encourage, and reward for which to customize a scoring formula;
ii) determining an individual raw magnitude of every scoring action $m_i$;
iii) assigning a distance value, determined by the distance from the opponent at which a scoring attack was executed, to a $D_{z_i}$ constant.
iv) assigning a placement value, determined by a scoring impact zone l on the combatants, to a $P_{l_i}$ constant;
v) assigning an independent combination bonus multiplier value to $C_1$ constant;
vi) assigning a magnitude, inclusive or exclusive of any modifying variable, per preference, of any desired scoring action to $A_1$ constant;
vii) assigning a magnitude, inclusive or exclusive of any modifying variable, per preference, of any desired scoring action to $A_2$ constant;
viii) assigning a time-dependent combination bonus modifier to $C_2$ constant;
ix) determining the amount of time elapsed between any scoring action and a previous scoring action $t_i$;
x) assigning a value, of a threshold of elapsed time between scoring actions eligible for application of combination scoring augmentation, to $T_n$ constant; and
xi) evaluating for $M_s$ and attributing to the relevant combatant to affect status of the match or game mode.

The resulting calculating method is defined as follows:

$$M_s = D_{z_i} m_i P_{l_i} + C_{1_n}\left(\frac{D_z A_1 + D_z A_2}{2}\right)\left(C_{2_n} - \frac{t_i}{T_n}\right) \Big| 0 < t_i \le T_n$$

| Definitions | |
|---|---|
| $M_s$ | Scoring magnitude of scoring action |
| $D_{z_i}$ | Zone of distance from opponent at which a scoring attack is executed |
| $m_i$ | Impact intensity of scoring action |
| $P_{l_i}$ | Placement modifier determined by location |
| $A_1$ | Magnitude of any desired scoring action |
| $A_2$ | Magnitude of any desired scoring action |
| $C_{1_n}$ | Independent combination bonus multiplier |
| $C_{2_n}$ | Time dependent combination bonus modifier |
| $t_i$ | Time elapsed between scoring actions |
| $T_n$ | Timer of scoring actions eligible to be augmented fey combination bonus |
| i | Pertaining to the selected scoring action in sequence |
| n | The number of scoring actions while t < T, reset to 0 when t ≥ T |
| $t_i$ | Location value attributed to striking zones |

| Constants | | | |
|---|---|---|---|
| Constant | Preferred Value | Preferred Definitions | Range |
| $D_{z_i}$ | 1 | f(z) | Real finite numbers |
| $P_{l_i}$ | Trunk = 1, Head = 2 | Arbitrary | Real finite numbers |
| $A_1$ | $M_{s_{i-5}}$, $m_i P_{l_i}$, $m_{i-1} P_{l_{i-5}}$ | $f(M_{s_{i-5}})$, $f(m_i, P_{l_i})$, $f(m_{i-1}, P_{l_{i-5}})$ | Real finite numbers |
| $A_2$ | $A_1$, $M_{s_{i-4}}$, $m_i P_{l_i}$, $m_{i-1} P_{l_{i-5}}$ | $A_1$, $f(M_{s_{i-4}})$, $f(m_i, P_{l_i})$, $f(m_{i-1}, P_{l_{i-5}})$ | Real finite numbers |

-continued

| Constants | | | |
|---|---|---|---|
| Constant | Preferred Value | Preferred Definitions | Range |
| $C_{1_n}$ | 1 | f(n) | Real finite numbers |
| $C_{2_n}$ | 1 | f(n) | Real finite numbers |
| $T_n$ | 1 | Arbitrary | Positive real numbers |

| $C_{1_n}$ Table | |
|---|---|
| n | $C_1$ |
| 1 | 0 |
| ... | ... |

| $C_{2_n}$ Table | |
|---|---|
| n | $C_1$ |
| 1 | 1 |
| ... | ... |

| $D_z$ Table | |
|---|---|
| z | D |
| 1 | ... |
| ... | ... |

| $T_n$ Table | |
|---|---|
| n | T |
| 1 | ... |
| ... | ... |

| $P_l$ Table | |
|---|---|
| l | P |
| Trunk | ... |
| Head | ... |
| ... | ... |

In a preferred embodiment, the following substitutions, definitions and simplifications yield the preferred of the many various final scoring equation possibilities:

$$M_s = D_{z_i} m_i P_{l_i} + C_{1_n}\left(\frac{D_{z_{A1}} A_1 + D_{z_{A2}} A_2}{2}\right)\left(C_{2_n} - \frac{t_i}{T_n}\right) \bigg| 0 < t_i \le T_n$$

Define:

$C_1 = 1, C_2 = 1, D_z = 1, T_n = 1,$ $A_1 = A_2 = m_i P_{l_i}, P_{l_{Trunk}} = 1, P_{l_{Head}} = 2$ $$M_s = 1 * m_i P_{l_i} + 1\left(\frac{1 * m_i P_{l_i} + 1 * m_i P_{l_i}}{2}\right)\left(1 - \frac{t_i}{1}\right)$$

$$M_s = m_i P_{l_i} + m_i P_{l_i}(1 - t_i)$$

In an exemplary embodiment, a calculation to determine the final magnitude of a scoring action is then performed by a computing device using the following method:

$$M_s = m_i P_{l_i} + m_i P_{l_i}(1 - t_i)$$

In this exemplary embodiment: $M_s$ represents the final magnitude of the scoring action, comprised of a single or multiple scoring impacts, $P_{l_i}$ represents the placement modifier (or multiplier) coefficient determined by the scoring impact zone on the opponent, wherein the most preferable embodiment allocates a value of 1 to an impact to the trunk and a value of 2 to an impact to the head, $m_i$ represents the raw magnitude of the impact, and $t_i$ represents elapsed time since the last scoring impact from the respective contestant. The purpose for introducing the variable $t_i$ into this scoring model is to include a consideration for the timing of a scoring impact in relation to other scoring impacts, which is not present in any combat sport, to benefit the contestant who scores consecutively within the 1 second allowed in the $(1 - t_i)$ component. Therefore, the lower the $t_i$ value, the higher the combination bonus awarded for that action, relative to that action. Because the variable $t_i$ is technically undefined until the second scoring impact per contestant per round, it will by default in each round be defined as equal to $T_n$ until it can be defined as an independent value. The function of the combination bonus is to objectively, quantitatively, and commensurately reward the behaviors which make the match exciting and intuitive to spectate. The more consecutive scoring impacts performed in combination, and the chronologically closer the scores within the combinations, the more and better combination bonuses a contestant will acquire, thereby rendering a quantitative stylistic advantage to the more intense contestant and discouraging conservative fighting.

Other advantages of the present disclosed subject matter will become apparent to the reader and it is intended that these advantages are within the scope of the present subject matter. To the accomplishment of the above, this disclosed subject matter may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE FIGURES

Various other features and attendant advantages of the present subject matter will become fully appreciated as the same becomes better understood when considered in conjunction with the accompanying drawings, in which like reference characters designate the same or similar parts throughout the several views, and wherein.

DETAILED DESCRIPTION

Figure 1:
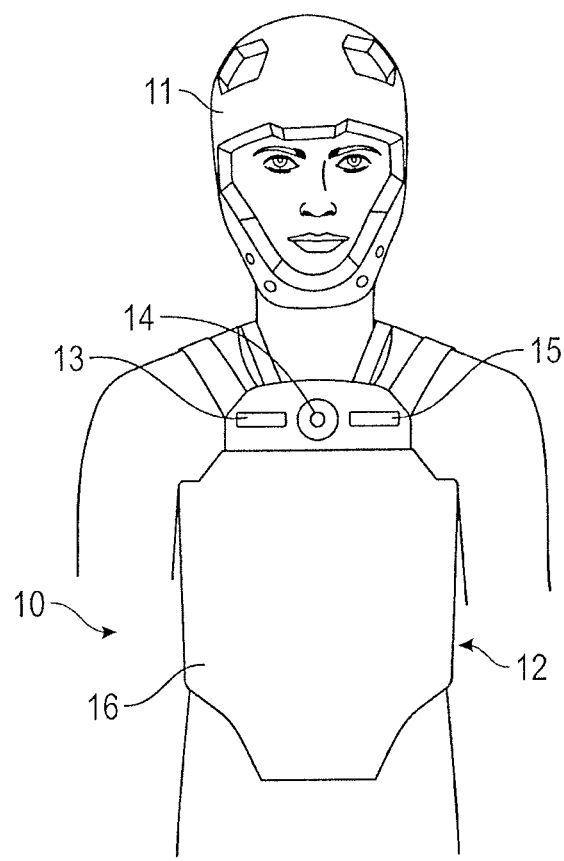
FIG. 1 depicts an exemplary embodiment of electronic protective gear worn by each player including a head protector and chest protector (or trunk protector or body protector) housing impact sensors and a graphical display, which comprise one player's portion of the data collection and display system.

Turning now to the Figures, FIG. 1 illustrates a data collection and display system 10 for generating and analyzing data relevant to combat match scoring, comprising a head protector 11 and chest (trunk or body) protector 12 used by a combatant/contestant. In taekwondo, a match typically includes a contestant designated the color blue "blue contestant" and a contestant designated the color red "red contestant". In the Figures, the Blue and Red designations will be used to designate opponents although other contestant designations may be used. The chest protector 12 further comprises a display area with a blue contestant health display, in this embodiment in the form of a blue contestant health display horizontal bar 13, a time display to display the time left in a round of a match, in this embodiment in the form of a time display ring 14, and a red contestant health display, in this embodiment in the form of a red contestant health display horizontal bar 15. The chest protector 12 further comprises a chest protector impact sensor zone 16. The chest protector impact sensor zone 16 is comprised of nanocomposite foam 16-1 sandwiching a conductive mesh conduit 16-2 (See FIG. 2).

Figure 3A:
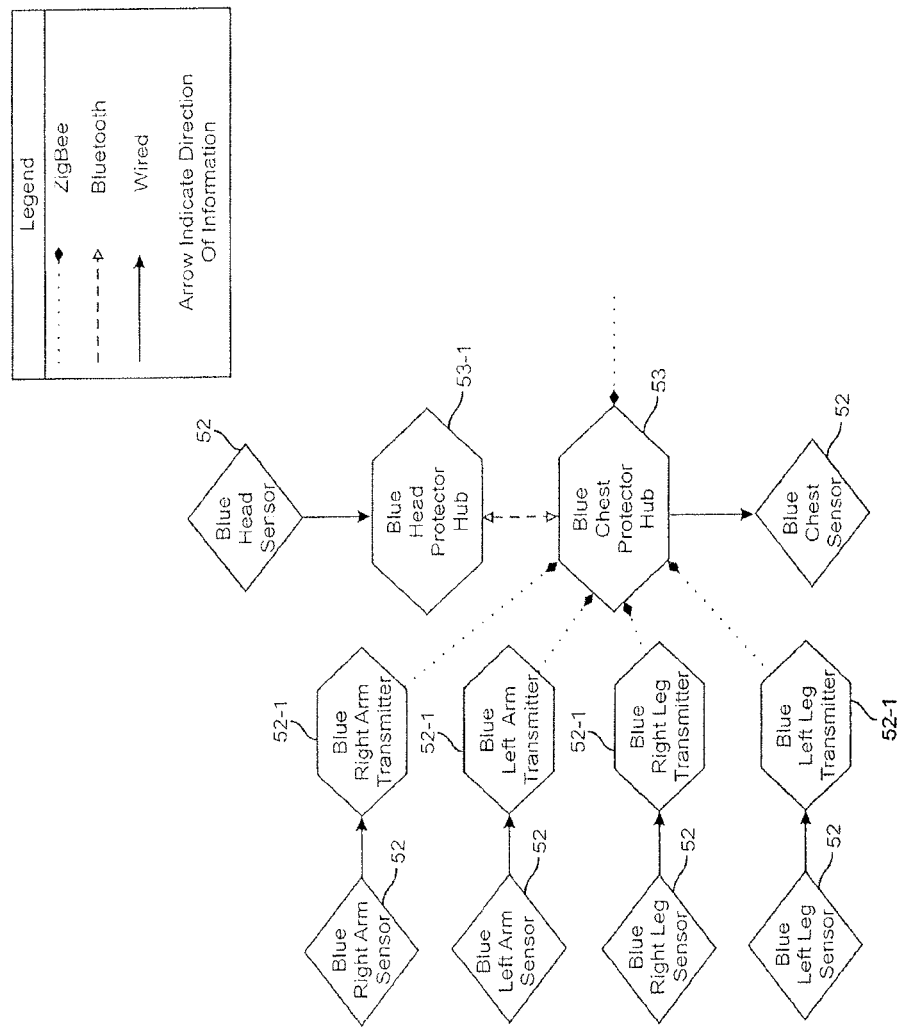
FIG. 3(A) and FIG. 3(B) depict exemplary embodiments of the components of the data collection and display system and the data connections between them wherein each of the body protector hubs only transmit data to each other.
Figure 3B:
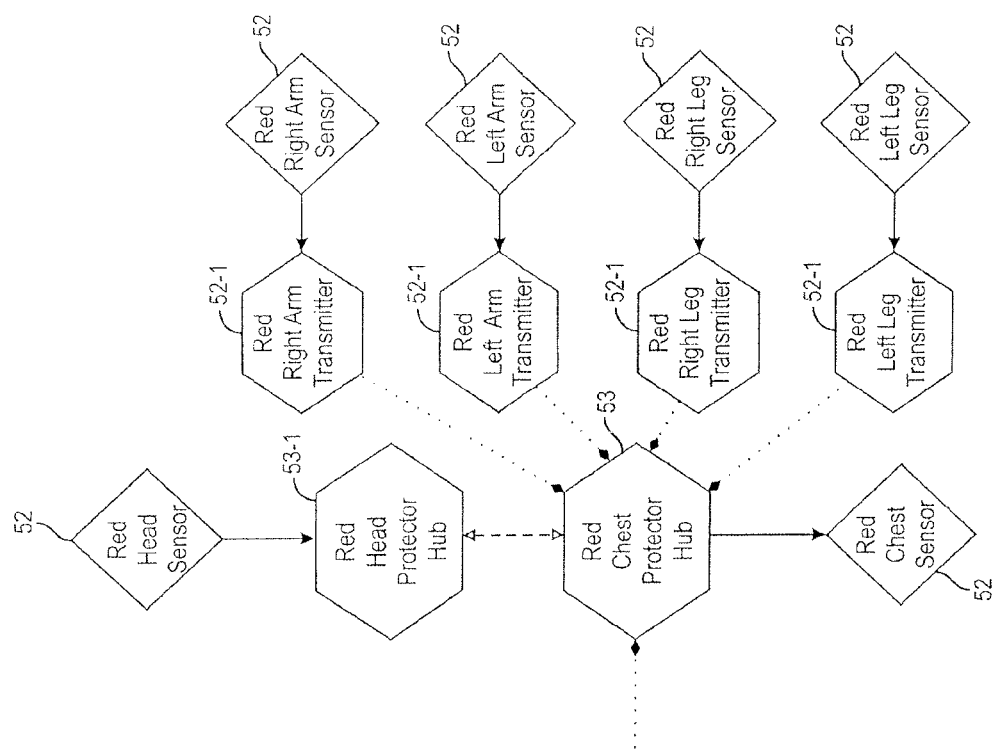
Figure 4A:
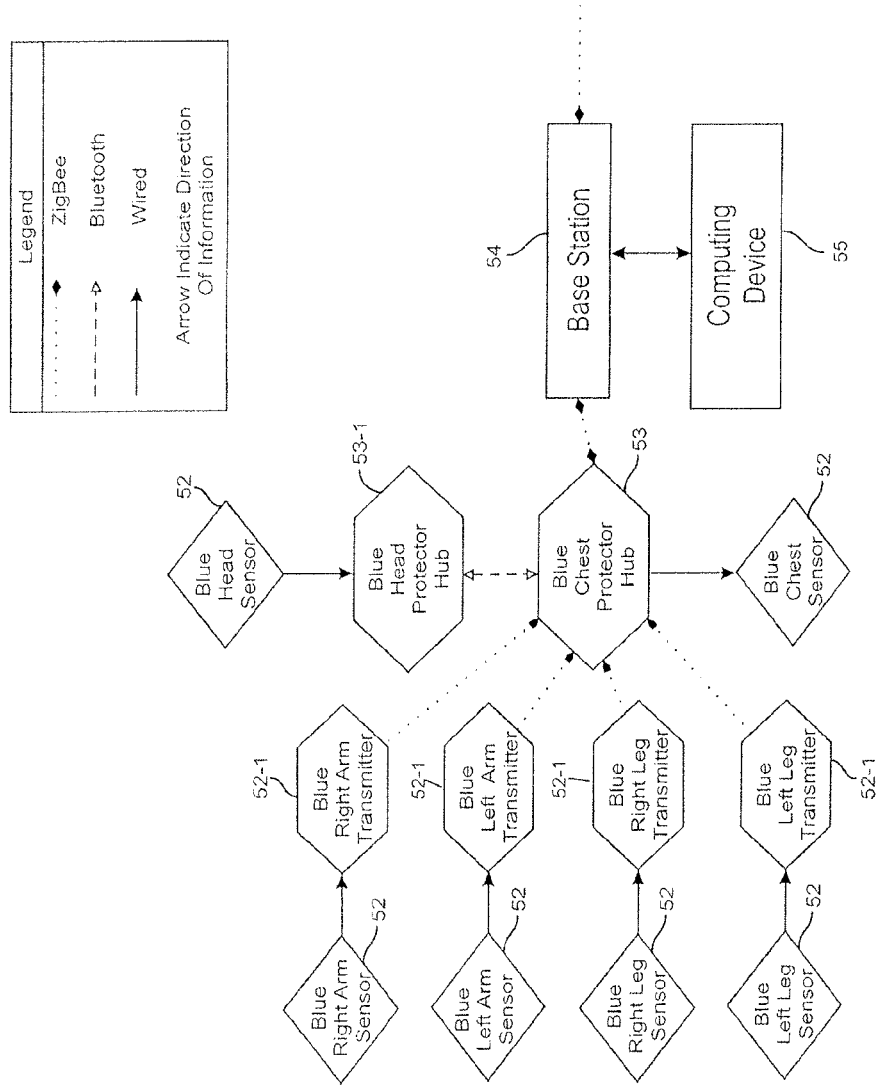
FIG. 4(A) and FIG. 4(B) depict exemplary embodiments of the components of the data collection and display system in which each of the body protector hubs communicate with an external computing device.
Figure 4B:
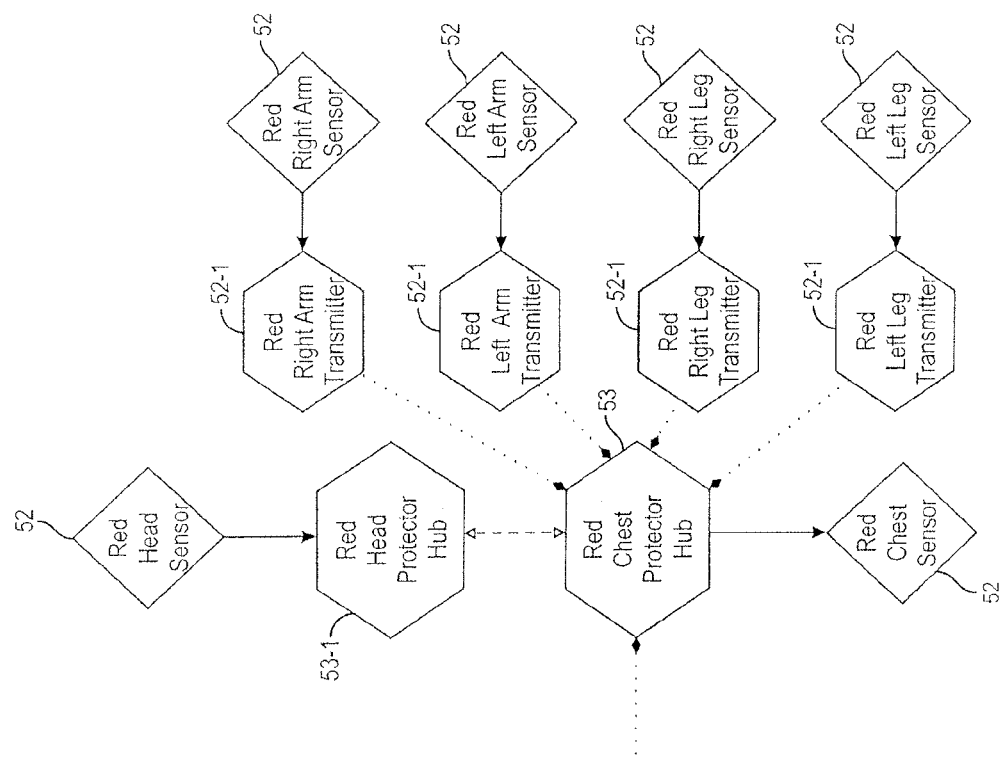

The data collection and display system 10 comprising the chest protector 12 (and head protector 11) including at least one body-worn sensor 16 or plurality of body-worn sensors on each contestant or combatant connected to a computing system 53 or 53-1 (See FIGS. 3 and 4) for collecting and analyzing data pertaining to quantitative properties within the parameters of sport specific events, such as, but not limited to, parameters of scoring actions, and for applying this data to affect the state (status) and score of the match of a combat sport. In an exemplary embodiment, the computational system is integral with the chest protector 12 or head protector 11 (FIG. 3). In another an exemplary embodiment, the computational system is distant the chest protector 12 or head protector 11 (FIG. 4).

Figure 2:
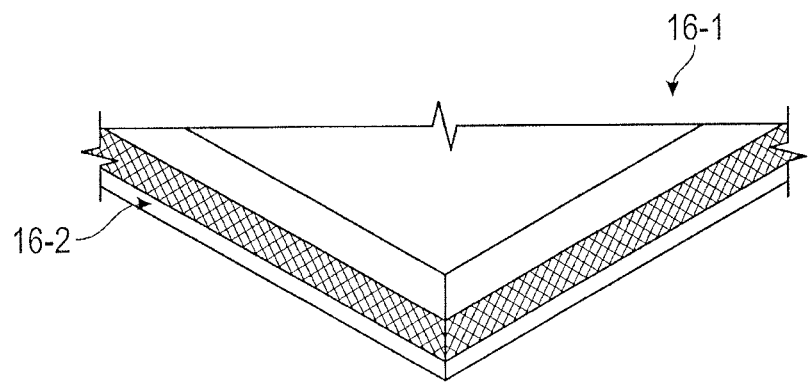
FIG. 2 depicts an exemplary embodiment in which conductive mesh is embedded into a sensitive foam comprised of conductive nanoparticles deposited into an elastomeric foam matrix to form a voltaic impact sensor and forming part of the trunk protector.

One class of such sensor 16 worn on the body performs a function of capturing data on the intensity of impacts experienced by the wearer (or combatant or contestant or player). The preferred embodiment of this sensor class measures impact energy absorbed by the sensor and takes the form of any triboelectric composite sensor wherein a plurality of conductive nanoparticles is deposed in a polymeric or elastomeric matrix to produce a voltage or variance in conductivity when impacted, such as in U.S. Pat. No. 8,984,954 B2, as shown in FIG. 2, and may possess a Conductive Mesh Conduit 16-2 to carry voltages embedded in nanocomposite foam 16-1. In the preferred embodiment, this class of sensor is applied in multiple discrete units, typically, but not always, consisting of a head protector 11 to gather data pertaining to the wearer's head, and a chest protector 12 to gather data pertaining to the general body of the wearer. Also in the preferred embodiment, the sensor also functions as a protective gear element, which protects the wearer from impacts related to the combat sport.

In another embodiment, the conductive material is non-mesh like. Preferably flat planar sheet like with conductive properties as above.

Another embodiment of such a sensor may take the form of a piezoelectric sensor, such as piezoelectric cable or piezoelectric film readily available from Measurement Specialties, Inc. Other embodiments may use any other types of sensors able to directly or indirectly measure strain or rate of strain including, but not limited to, piezo resistive sensors, load cells, transducers, and strain gauges. In any of these embodiments, the sensor may be affixed to or integrated into a protective gear element such as a head protector 11 and/or chest protector 12.

Another embodiment is comprised of more or less than two units of such sensors, which may be placed anywhere on the wearer including, but not limited to, head, trunk, hands, feet, groin, back, arms, and legs.

A second class of sensor worn on the body performs a function of quantifying the mechanics (or mechanics-class sensor) of the wearer's body and limb movement including, but not limited to, angular and rectilinear position, velocity, and acceleration of the hands, feet, general body, head, elbows, and knees. In the preferred embodiment, this sensor class takes the form of multi-axis electronic accelerometers and gyroscopes positioned on the hands, feet, and trunk, and are affixed to or integrated into protective gear such as arm guards and shin guards (See FIG. 4(C) and FIG. 4(D)).

Another embodiment of such a sensor takes the form of a compass, GPS tracker, or any other instrument capable of directly or indirectly measuring an object's angular or rectilinear position, velocity, or acceleration in space. Another embodiment of such a sensor takes the form of any device or sensor capable of directly or indirectly measuring the relative magnitude of acceleration in an impact event, including, but not limited to the types of strain and strain rate sensors mentioned above.

The computing system (or hub) 53, as best seen in FIGS. 3 and 4, is connected to each sensor 52 (each leg and arm sensor being connected to a transmitter 52-1 to transmit to the chest protector hub 53, the head sensor 52 is connected directly to the head protector hub 53-1 which communicates with chest protector hub 53, the chest sensor is connected directly to the chest protector hub 53), wirelessly (such as ZigBee™ or Bluetooth™) or by a data bus, and is capable of reading each sensor and performing calculations and logical operations to determine, from collected data, changes to the status and statistics of match parameters, including, but not limited to, health points, end of round or match, and kinematics of players.

In FIG. 3, the computing system is the chest protector hub 53 that calculates all match-relevant parameters without connection to an external computing device and the Blue system is in wireless communication with the Red system. In this instance, the wireless communication is through ZigBee™.

In an exemplary embodiment shown in FIG. 4, the mechanics-class sensors 52 and the Head Protector impact sensor 52 on each player are all connected to their own, separate satellite signal processor circuits/transmitters 52-1 which are capable of short-range wireless transmission of the raw data from the respective sensor in an analog or digital form to the chest protector hub 53. Also in the preferred embodiment, a small processor/hub capable of receiving and transmitting data at a longer range is attached to, or integrated into, clothing or gear on the wearer's trunk. Also in this exemplary embodiment, the chest protector impact sensor 52 is connected by data bus cable to the small processor/hub 53. This exemplary embodiment may also include one or more personal computers, handheld computing devices 55, or other devices with a graphical user interface (i.e. mobile device) which allow someone not competing in the match, including, but not limited to a referee, judge, or spectator, either in location or remotely, to view and/or alter aspects of the match status and statistics parameters, including, but not limited to, health points, clock, raw sensor data, and any other match parameter named in this document. A mobile device may also incorporate both base station 54 and computing device 55. As shown in FIG. 4, the chest protector hub 53 is connected with base station 54 and computing device 55. Also in this exemplary embodiment, the chest protector 12 may feature graphical or other indicators to display match parameters on the contestant such as blue contestant health 13, time ring 14, and red contestant health 15 (See FIG. 1).

In other embodiments, sensor data may be communicated by any electronic or optical means to any type of processor capable of receiving sensor data by the chosen media and applying logical and mathematical operations to relate sensor data to appropriate and logical changes in the state of the match, such as, but not limited to, health points and clock.

Figures 4C, 4D:
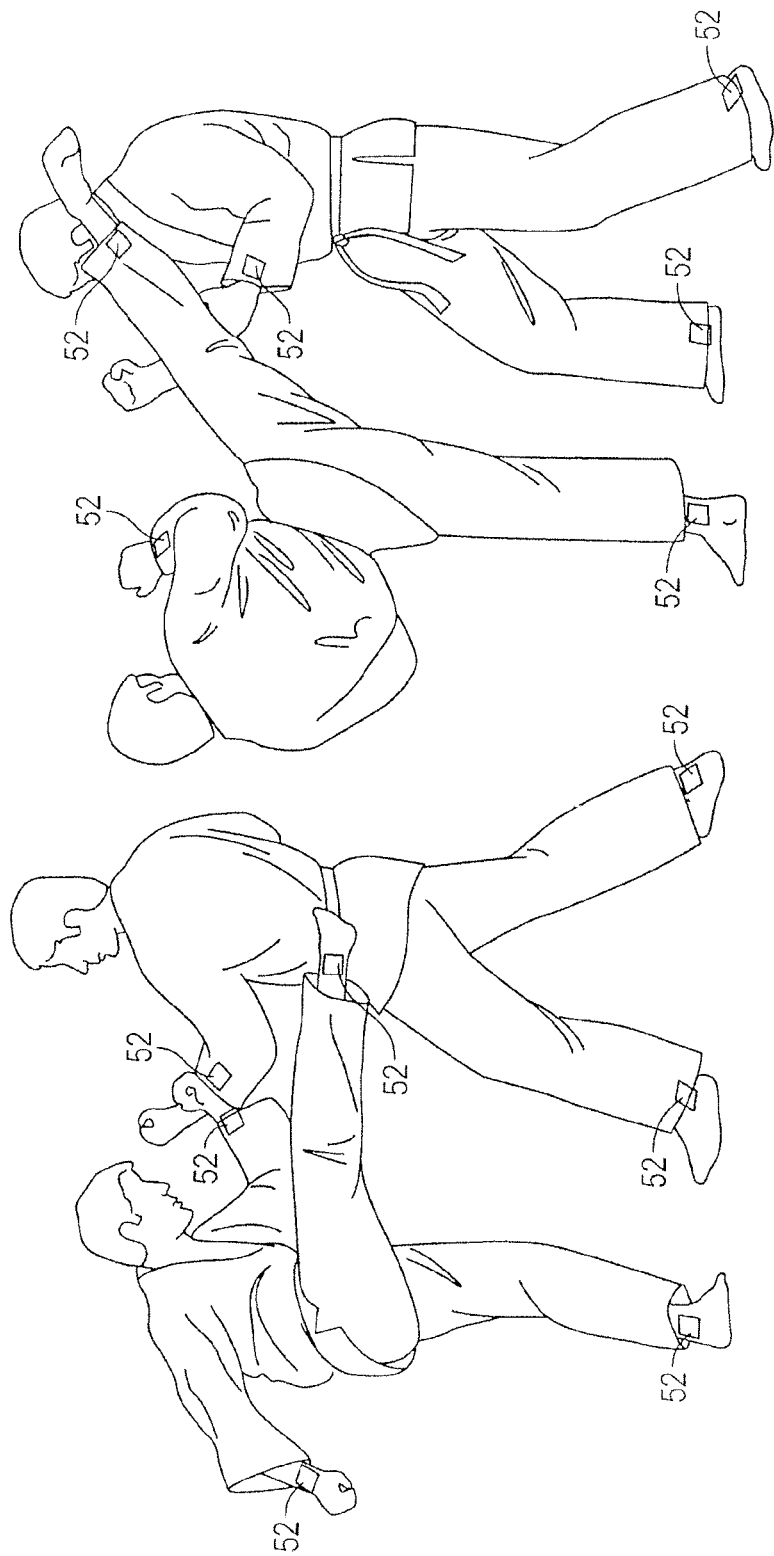
FIG. 4(C) and FIG. 4(D) depict two combatants with motion sensors on their hands and feet.

FIG. 4(C) and FIG. 4(D) depicts two opponents in a combat match scenario. Each opponent has motion sensors 52 on their hands and feet to track the motion thereof. On the left A, the motion sensor has tracked the motion and trajectory of the right foot of a player executing a kick to the body of another player. On the right B, the motion sensor has tracked the motion and trajectory of the right foot of a player executing a kick to the head of another player.

Figure 5:
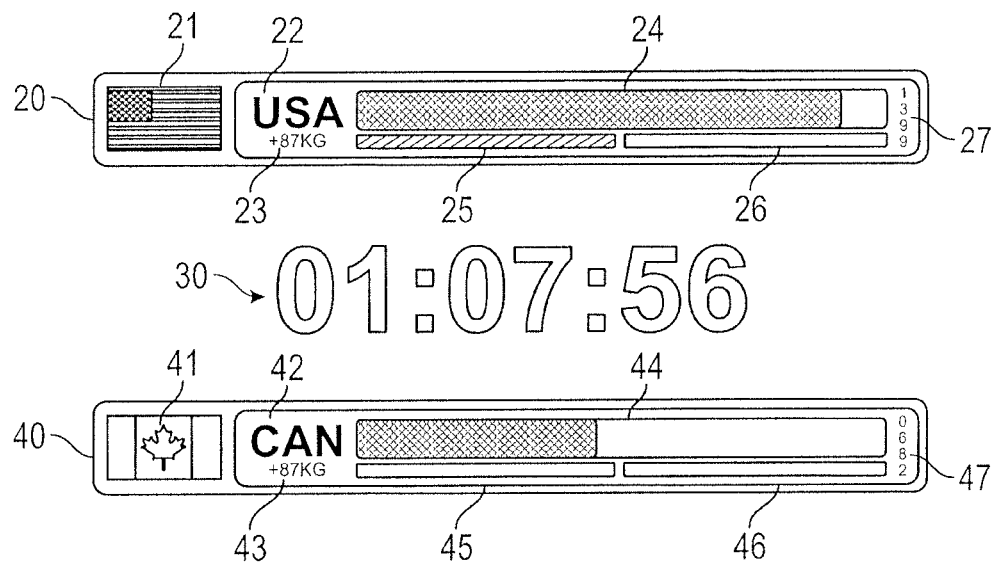
FIG. 5 depicts an exemplary embodiment of a graphical display system in an active-match state, detailing a circumstance with 1 minute, 7.56 seconds remaining in the second round of play or combat match.
Figure 6:
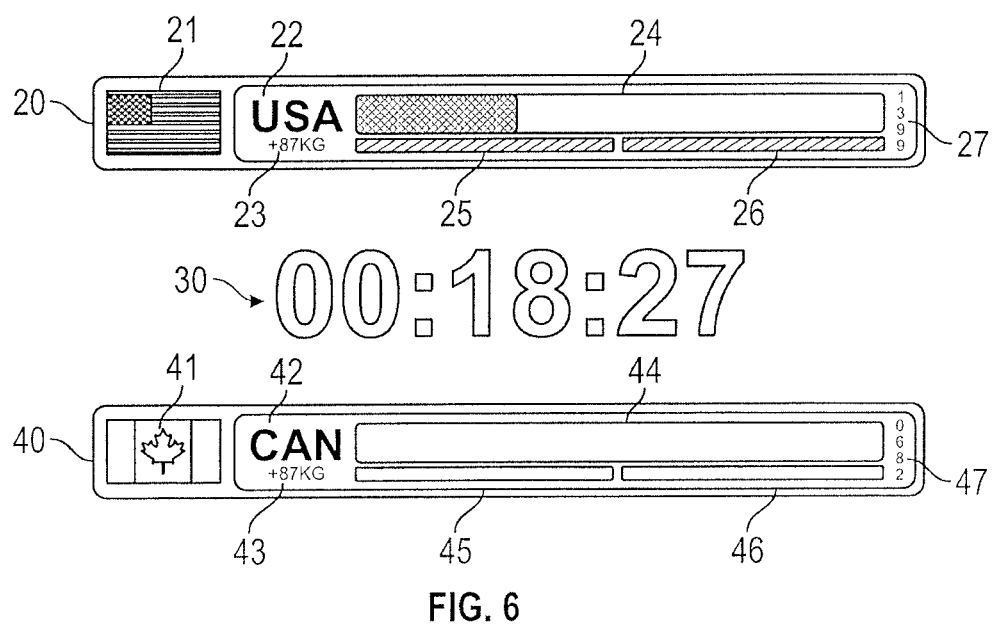
FIG. 6 depicts an exemplary embodiment of the graphical display system in a post-match state, detailing a circumstance wherein "Blue" has successfully depleted the opponent's "Red" health points with 18.27 seconds remaining in the second round of a match, at the instant of granting "Blue" a second round victory and declaring "Blue" the victor of the combat match.

FIGS. 5 and 6 depict an overall contestant and match information display (which may be displayed on the display are of the chest protector, a monitor, a computer, a hand held device, a tablet or mobile device) including a blue contestant status indicator 20 for providing the audience, referee, and players with information pertinent to the contestant designated "Blue", a clock 30 for detailing the time remaining in the current round, and a red contestant status indicator 40 for providing the audience, referee, and players with information pertinent to the contestant designated "Red". The blue contestant status indicator 20 in this embodiment is a form of display graphically structured as an elongated bar encapsulated in any aesthetically desired shape, comprised of vital and assistive information pertaining to "Blue" for the function of providing information visually to the contestants, referee, and audience. The shape and layout of the blue contestant status indicator may be varied as desired.

The blue contestant status indicator 20 displays vital and assistive information associated with the blue contestant. Vital information is shown as: blue contestant health bar 24, blue contestant round victory indicator one 25, blue contestant round victory indicator two 26, and blue contestant health points 27. Assistive information not crucial to direct representation of the status of the match is shown in the most preferable embodiment as: blue contestant emblem 21, blue contestant country or team 22, and blue contestant weight category 23.

Possible variations of the blue contestant status indicator 20 are embodied in the optional assistive information, which may be presented in addition to, or in place of, the assistive information shown in the Figures. This includes, but is not limited to, name of contestant, name of event or sport, seeded rank, or stage of competition. Further variation from the preferred embodiment is exemplified by a number of round victory indicators 25, 26, equal to the number of rounds of which a match consists, or equal to the number of round victories equal to the number required for total match victory.

The clock 30 serves to inform the contestants, referee, and audience of the time of play remaining in the round.

The clock 30 in this embodiment digitally denotes minutes, seconds, and hundredths of seconds. An analog version may also be implemented.

The red contestant status indicator 40 is a form of display graphically structured as an elongated bar encapsulated in any aesthetically desired shape, comprised of vital and assistive information pertaining to "Red" for the function of providing information visually to the contestants, referee, and audience.

The red contestant status indicator 40 displays vital and assistive information. Vital information is shown as: red contestant health bar 44, red contestant round victory indicator one 45, red contestant round victory indicator two 46, and red contestant health points 47. Assistive information not crucial to direct representation of the status of the match is shown in the most preferable embodiment as: red contestant emblem 41, red contestant country or team 42, and red contestant weight 43.

Possible variations of the red contestant status indicator 40 are embodied in the optional assistive information, which may be presented in addition to, or in place of, the assistive information shown in the figures. This includes but is not limited to, name of contestant, name of event or sport, seeded rank, or stage of competition. Further variation from the preferred embodiment is exemplified by a number of round victory indicators 45, 46 equal to the number of rounds of which a match consists, or equal to the number of round victories equal to the number required for total match victory.

Possible variations include more than two round victory indicators and may be determined as desired.

Both the blue contestant status indicator 20 and the red contestant status indicator 40 are composed of the same sub-elements within the outer border of the indicators: emblem 21, 41, country 22, 42, weight 23, 43, health bar 24, 44, round victory indicator one 25, 45, round victory indicator two 26, 46, quantitative health point values 27 47, and any optional assistive information.

As best seen in FIG. 5, in this case, the blue contestant has won the first round as shown by the round victory indicator 25, and the match is in the second round with 1 minute 7.56 seconds left (30) in the second round and the blue health bar 24 is greater than the red health bar 45.

As best seen in FIG. 6, in this case, the blue contestant has won both first and second rounds (25, 26) having depleted the red contestant's health bar 45 with 18.27 seconds left in the round.

Variations of the method and system include, but are not limited to: rotating the "health bars" to a vertical or other orientation, changing the geometric visual representation of the quantity of health points from a "bar" to any other aesthetically desired format, changing the maximum number of rounds to a number other than three, making the protocol of the game a count-up-to-a-cap system rather than a depletion system, making the protocol of the game a system of total comparative cumulative health points inflicted rather than a depletion system, and changing the contestant colors or designations.

Variations to the data collection and display system include, but are not limited to: varying the type or placement of sensors which perform the same intended functions, varying the electronic architecture and infrastructure, (such as varying connection type or network structure, communication media, and processor types and number), and changes in logical processing protocol toward the same general system functionality. One such change to electronic architecture is shown in FIG. 3 in which the body protector hubs calculate all match-relevant parameters without connection to an external computing device.

The present subject matter provides a system and method for conducting a combat sport, in which multiple players, such as a pair of opponents each designated "Red" and "Blue", are given a quantity of health points 27 47, wherein the object is to deplete those points of the opponent to a value of "0", as shown in FIG. 5, to achieve a round victory, or to successfully render the opposing contestant unconscious or incapacitated, by the use of legal techniques to achieve a match victory by knockout.

The quantity of points to be deducted from the receiving player is calculated by measuring the magnitude of a given impact with the impact sensor or sensors worn on the contestants and mathematically combining that magnitude with other factors as described below.

Raw impact data is generated by the impact sensors on each player or combatant and communicated, in a pre-filtered or raw state, to the on-board processor hub on each player, which may apply time stamps and additional filtering. Simultaneously, raw kinematic data is generated by the mechanics sensors on each player and communicated, in a pre-filtered or raw state, to the onboard processor hub on each player, which may apply time stamps and filtering. The processor hubs may, in an exemplary embodiment, communicate the filtered or raw data from all sensors to a computing device external to the worn gear (and in another exemplary embodiment, internally to an onboard hub or processor), which in turn applies mathematical and logical operations to the impact and mechanics data to determine when an impact above a specified threshold has been dealt to a player by another player using legal techniques, and the relative magnitude of the impact.

Health points equal to the final magnitude, $M_s$ (see discussion above) of the scoring action are deducted from the recipient player's Health Points 27, 47. Each player's Health Bar 24, 44 changes proportionately to reflect changes in the player's Health Points 27, 47 (See FIGS. 5 and 6). Similarly, the health displays 13, 14 on the trunk protector will change accordingly (see FIG. 1).

The health points of a contestant may also be modified by referee penalty for illegal actions. An exemplary embodiment involves three levels of penalties: minor penalties, major penalties, and disqualification. In an exemplary embodiment, minor penalties are equal to $\frac{1}{6}$ of the contestant's starting health points, major penalties are equal to $\frac{1}{3}$ of the contestant's starting health points, and disqualification or knockout yields an immediate revocation of any remaining health points in the current and remaining rounds and the match victory is awarded to the remaining contestant. Regardless of the number and kind of penalties received, any contestant with any health points remaining is still a contender in the round.

Variations of the referee behavior include any ability to modify score, administer penalties, or interact with relevant persons in the match as determined necessary to effectively administer and uphold the functions of the protocols defined herein. Such exceptions may include, but are not limited to, adding health to the opponent of the infracting player rather than inflicting penalty damage upon the infracting player, or a "strike" system wherein a player is given a limited number of infractions before disqualification with or without score modification in penalty.

If neither contestant succeeds in attempting to deplete the opponent's health points within the time allowed, the contestant with the higher quantity of health points at time "00:00:00" on the clock will be granted the round victory for that round. In the extremely unlikely circumstance that at time "00:00:00" on the clock both contestants have an identical quantity of health points, the referee shall declare which contestant was superior, according to whatever agreed upon criteria, and award the round to that contestant. In an exemplary embodiment, in the event that at the end of two rounds, both contestants have achieved one round victory each, an additional round designated "overtime" will be added to break the tie.

The victor of the match is decided by disqualification, by simple majority of round victories, or in the case of full contact status being agreed upon, by knockout. An exemplary embodiment conducts the match in a "best of three" format as applied by the protocol shown in FIG. 7, wherein if the same player wins the first two rounds, as shown in FIG. 6, a third round is not contested. In the case of a knockout considered legal under the agreed upon rules following this protocol, the remaining viable player is declared the victor of not only the round, but the entire match.

Figure 7:
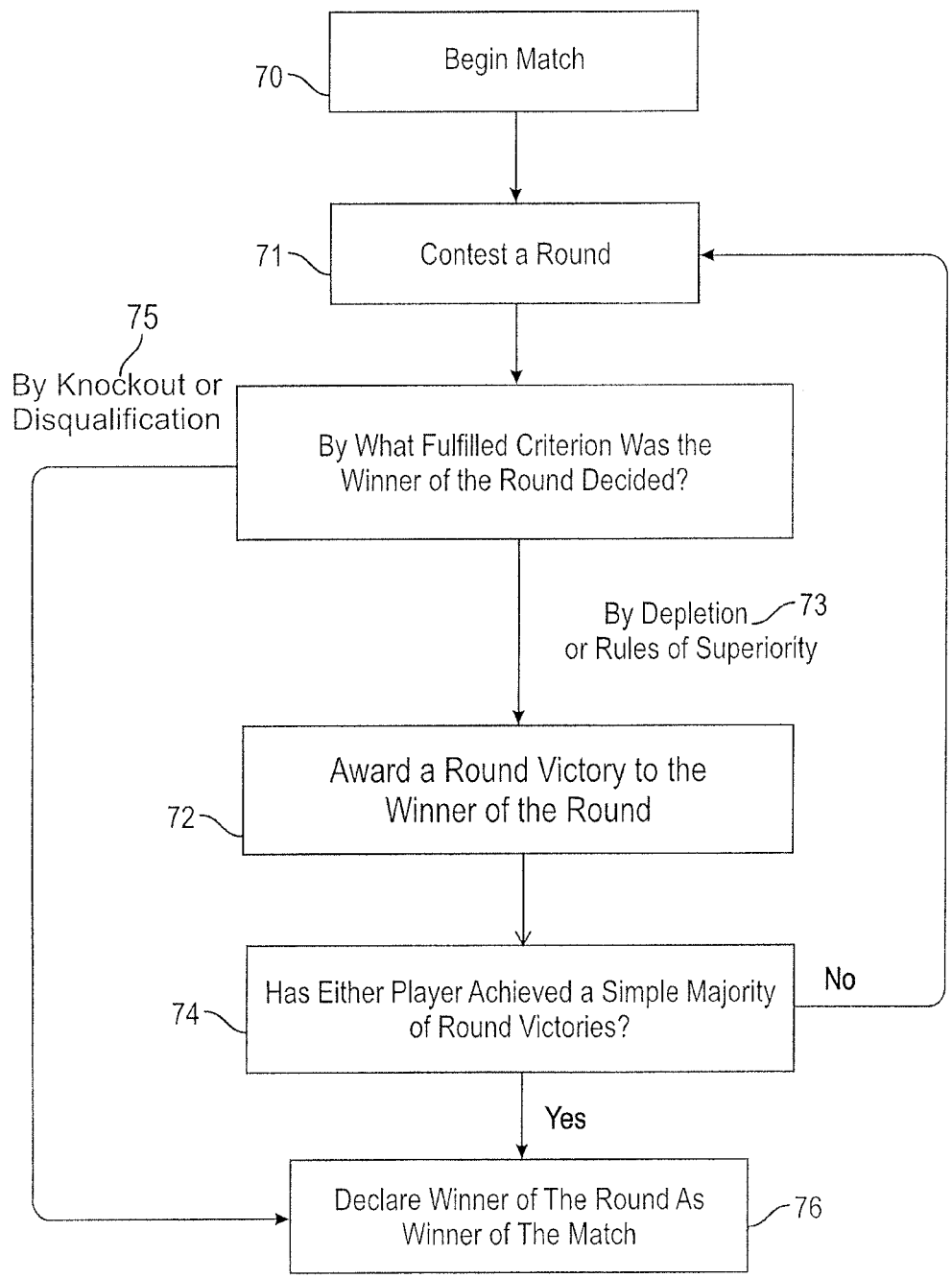
FIG. 7 depicts a flowchart illustrating the overall general protocol for contesting a match under an exemplary embodiment.
Figure 8:
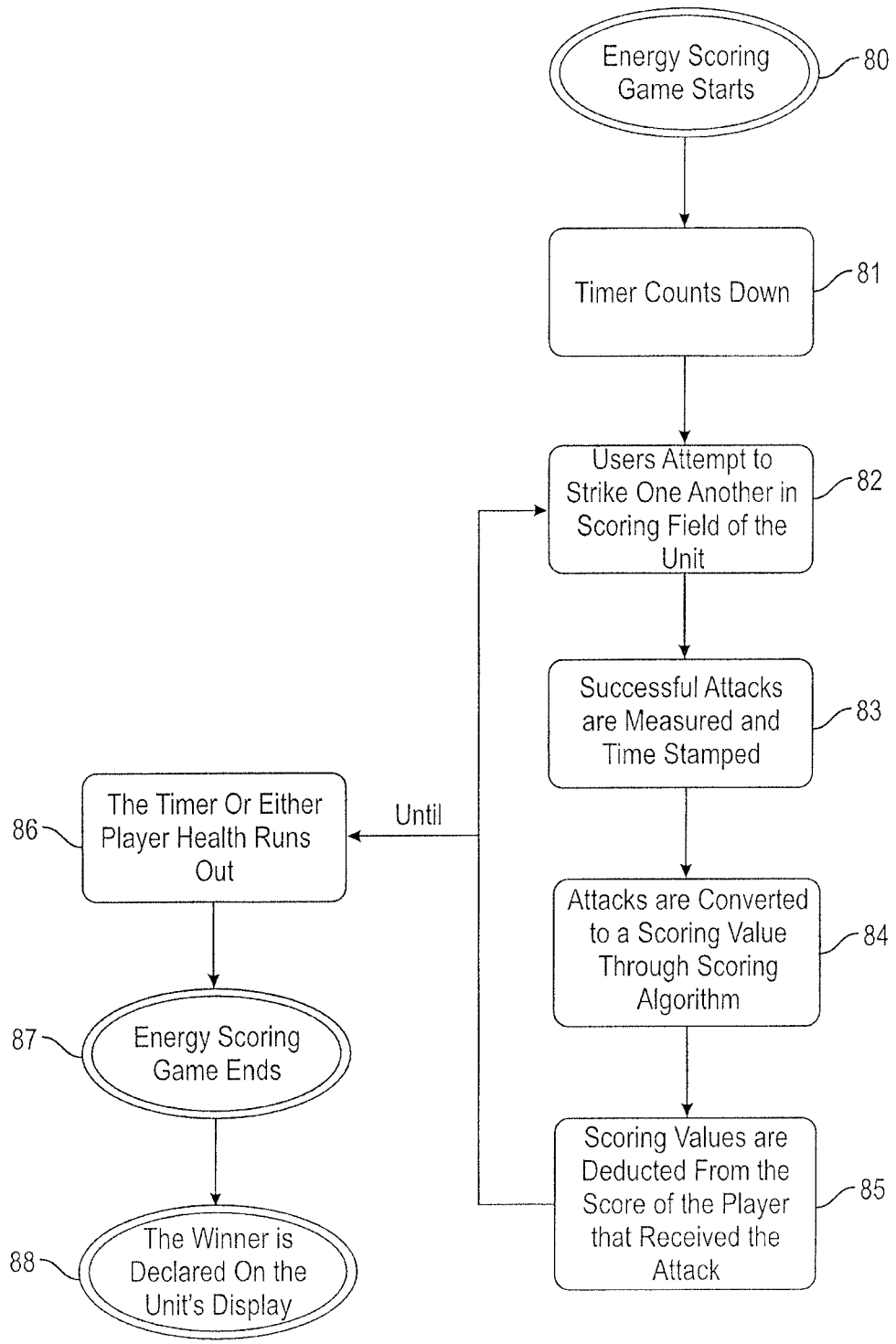
FIG. 8 depicts a flow chart illustrating an exemplary overall general protocol for contesting a match according to another exemplary embodiment.

Specifically referring to FIG. 7, one begins a match 70 with two players or combatants (participants), and a first round of a match is contested 71 and a round victory is awarded to the winner 72 of the round by depletion or rules of superiority 73, and the next decision is whether either player has achieved a simple majority of round victories 74, if no, one proceeds to a second round following the same protocol as the first round 71 until a player has achieved a simple majority of round victories 74. The other alternative is during any round, if a player is eliminated by knockout or disqualification 75, the winner is declared 76. Referring now to FIG. 8, there is provided another protocol for an energy scoring game between two players. The energy scoring game is initiated 80, the timer begins to count down 81 while the players/users attempt to strike in the scoring field of the unit (trunk protector or head protector) of the opponent 82. Successful attacks are measured and time stamped 83, converted to a scoring value based on the model discussed above by the computing device or microprocessor 84, with scoring values deducted from the score of the player receiving the attack or impact 85 until the times runs out or a player's health status is depleted 86, resulting in the energy scoring game ending 87 and a winner being declared and displayed on the chest protectors 88.

Figure 9:
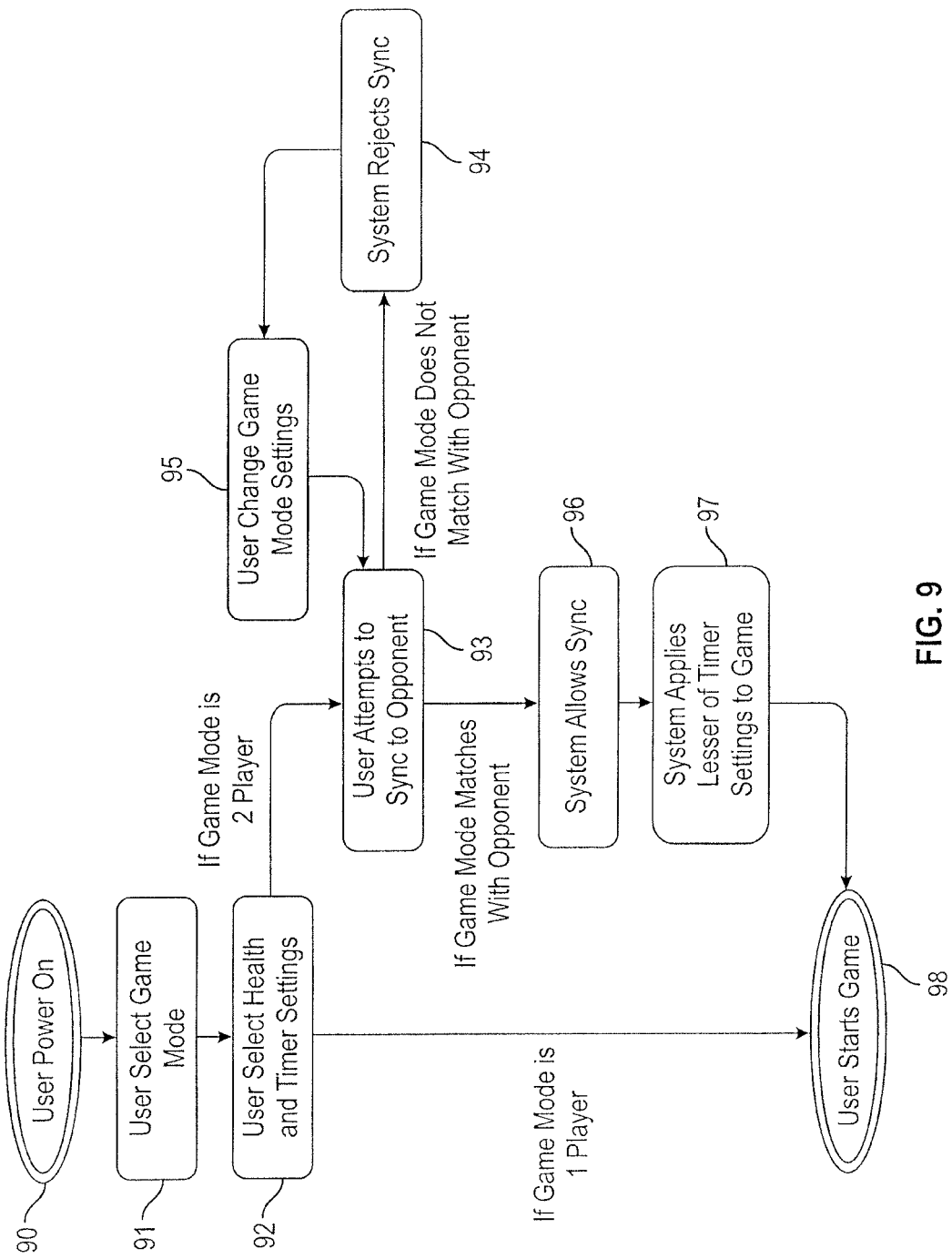
FIG. 9 depicts a flow chart illustrating exemplary steps involved when a user chooses a single player mode (for sole training) or two player mode.

Referring now to FIG. 9, there is provided a general protocol to initiate the system. A player/user powers on the unit via the control panel 90, the user selects a game mode 91 and health and timer settings 92. If the user/player chooses a 2-player mode, the user/player attempts to synchronize with the opponent 93, if the game mode does not match with the opponent game mode, the system will reject the synchronization 94 forcing a change in game mode 95 to attempt to synchronize with the opponent. If the game mode matches with the opponent, the system allows the synchronization 96, engages the timer 97 and starts the game/match/round 98.

Figure 10:
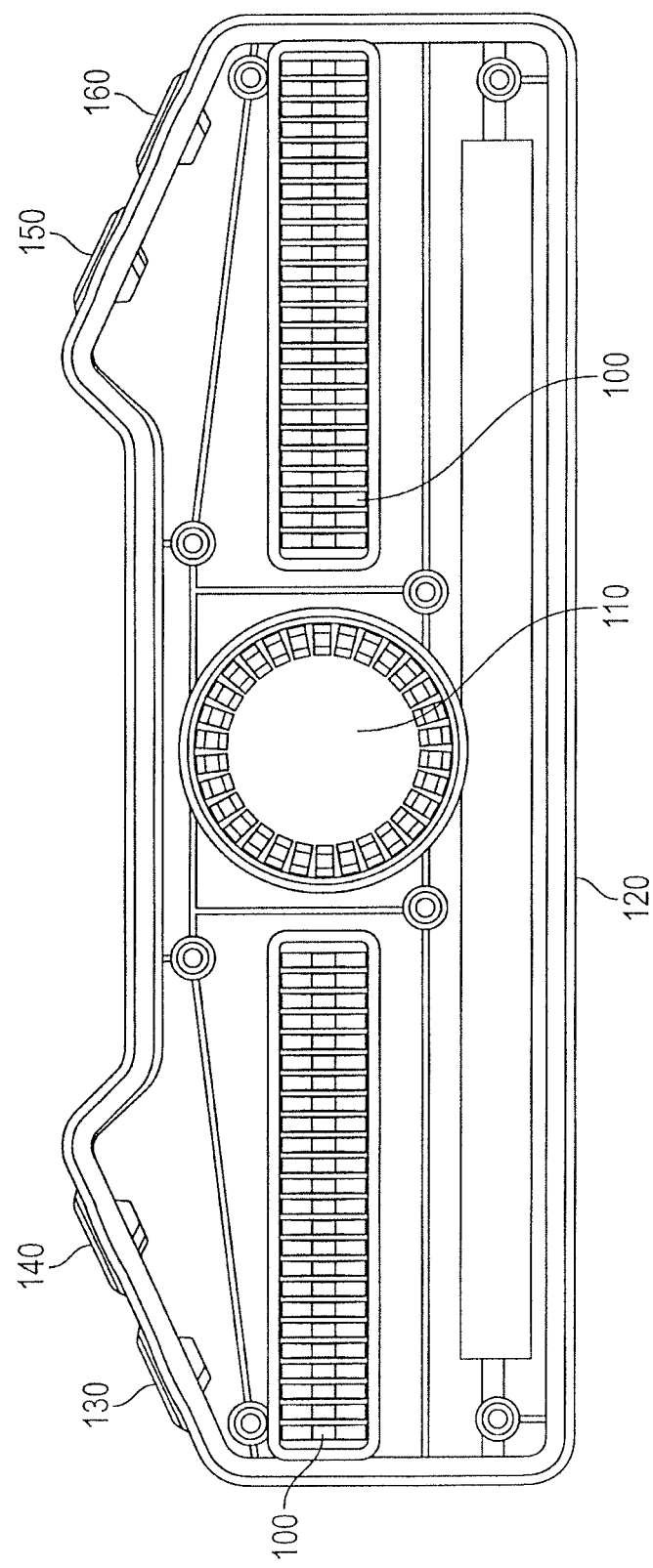
FIG. 10 depicts an exemplary player health and timer element insert for the chest protector forming the display area according to an exemplary embodiment.
Figure 11:
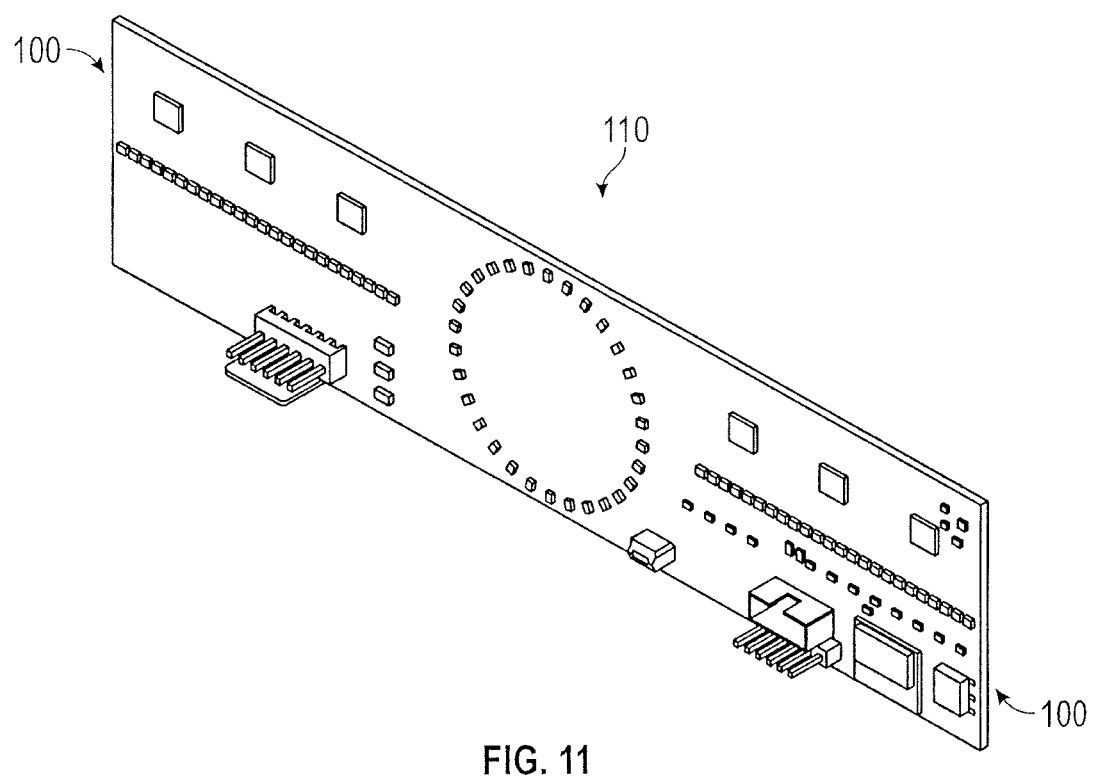
FIG. 11 depicts an exemplary printed circuit board of the player health and timer element of FIG. 10.

Referring now to FIGS. 10 and 11, there are depicted the player health bars 100 (for each player) and timer element 110 according to an exemplary embodiment. In this embodiment, the power source for the unit is a battery 120 integral with the health and timer trunk protector element. Also depicted are a health button 130 to regulate player health level, timer button 140 to regulate the timer, game mode button 150 to regulate type of game and play button 160 to control play on or off. This is similar to the player health and timer depicted in FIG. 1 as 13, 14 and 12 respectively. The player health and timer element, in particular the circuit board 170 is encased in an enclosure (See FIG. 12-1) to protect the electronic components and LEDS from sustaining damage due to an impact. In exemplary embodiments, the plastic enclosure 180 is then covered with a silicone covering 190 further protecting the health and timer element and related buttons, while allowing clear viewing of the health bars and timer on the chest or trunk protectors. FIG. 11 depicts the printed circuit board of the player health 100 and timer element 110. In particular, the health bars and timer element provide a visual indicia formed of individual RGB LEDS, preferably in series. However other lighting systems may be used.

Figure 12A:
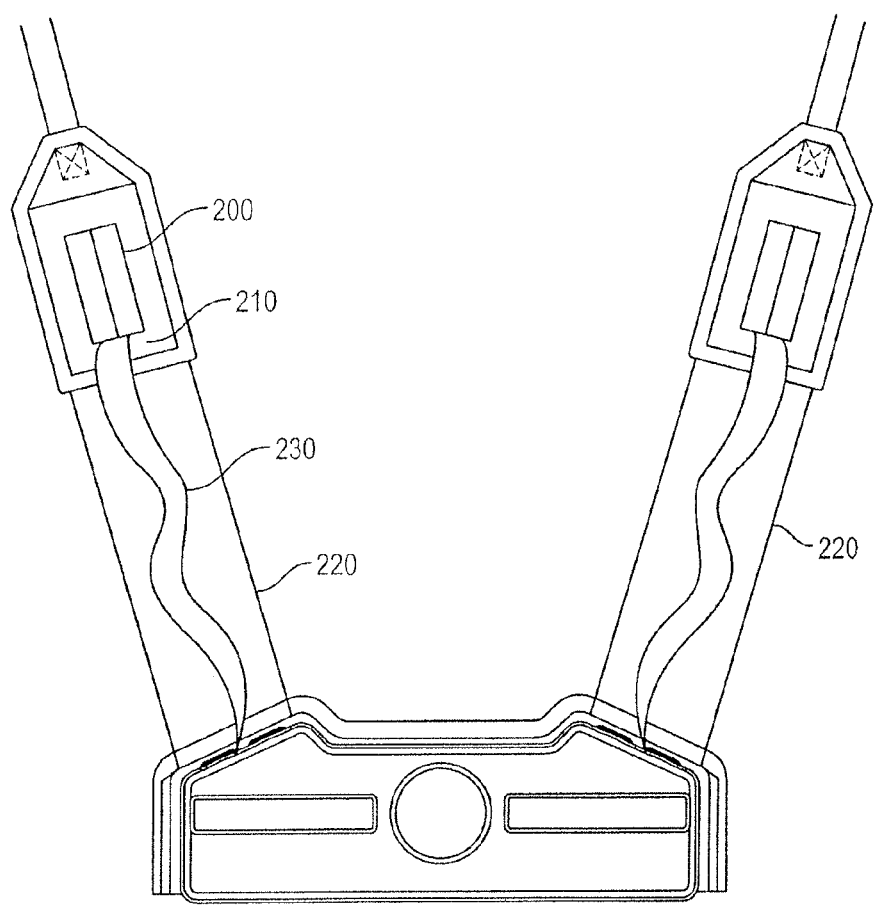
FIG. 12(A) depicts an exemplary connection of the player health and timer element to the chest protector according to an exemplary embodiment.
Figure 12B:
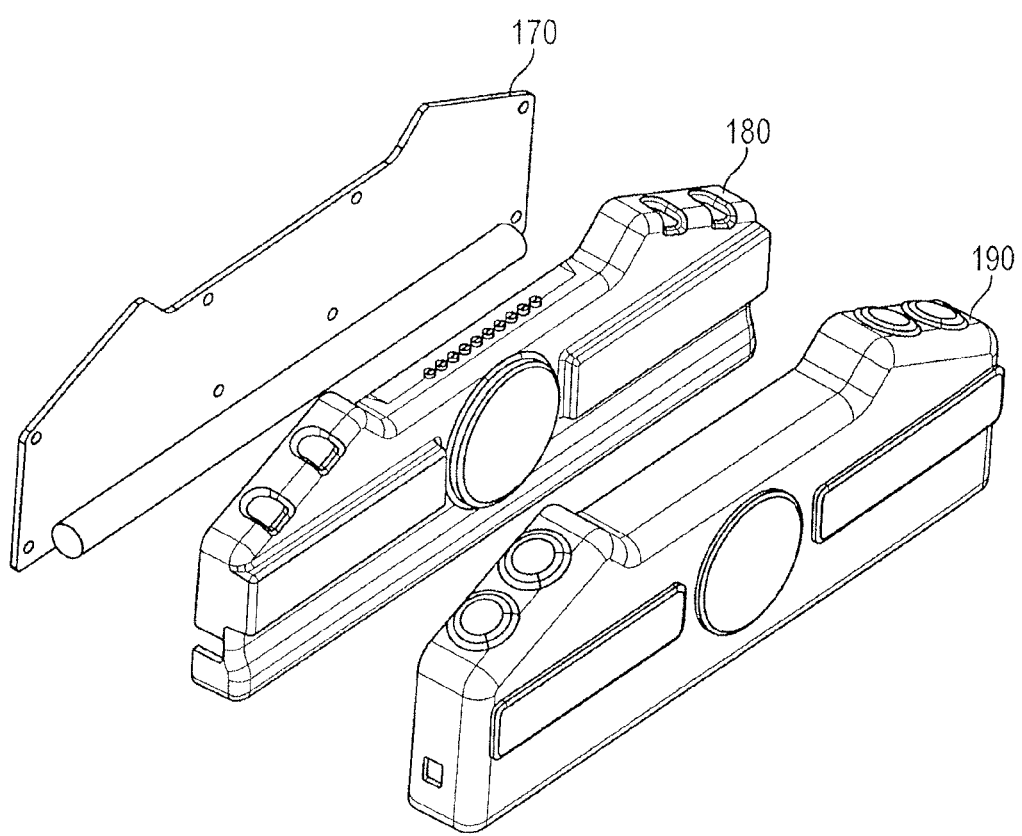
FIG. 12(B) depicts an exploded view of an exemplary display area.

FIG. 12 (A) and FIG. (B) shows an exemplary embodiment with the power source being in the form of a battery pack 200 in a battery pouch 210 found along one or both shoulder straps 220 of the trunk protector 12. The battery pack 200 is connected to the health and timer element by battery cables 230 running along the inside of the shoulder strap 220.

Figure 13:
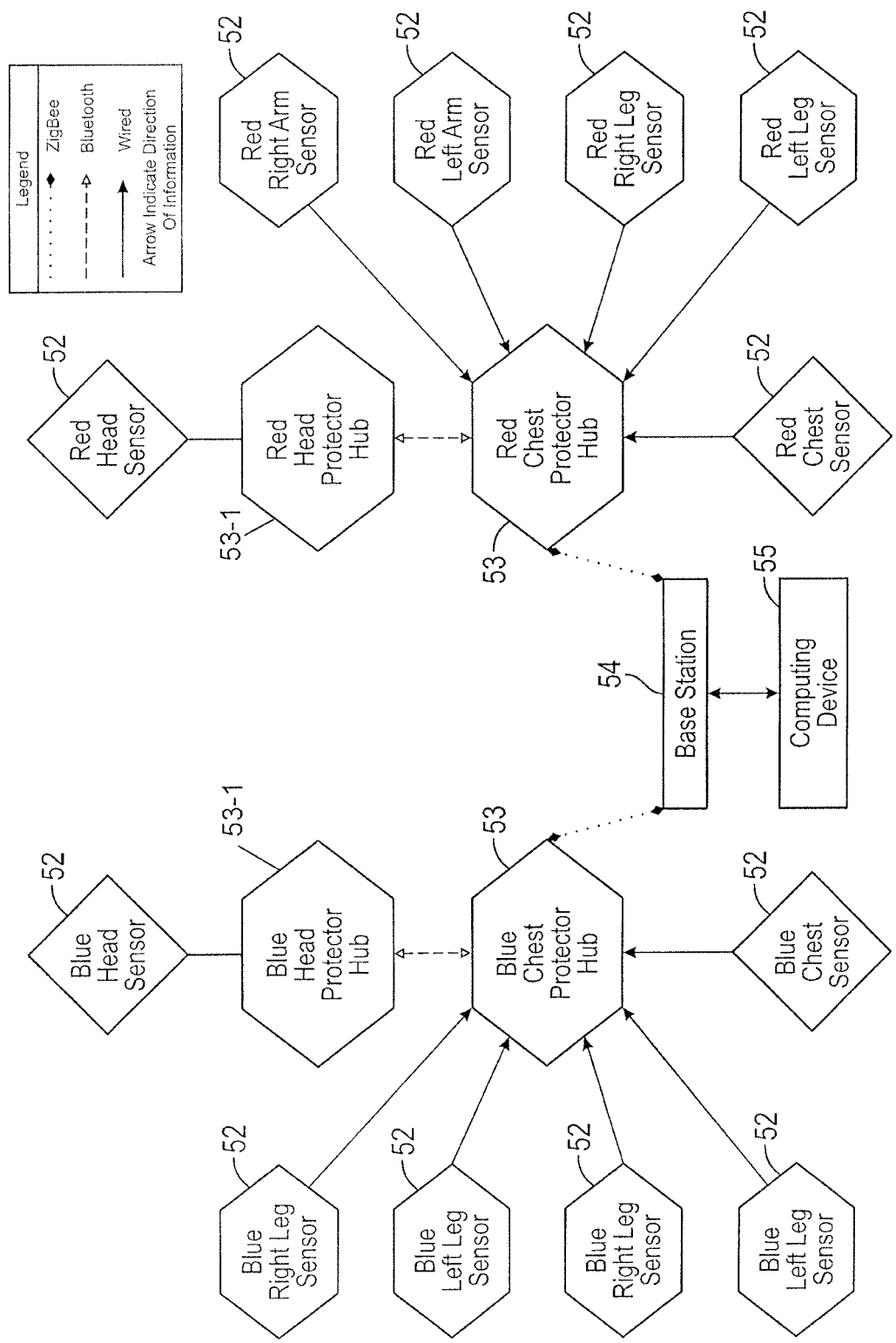
FIG. 13 depicts a variation of the components of FIG. 4 of an exemplary data collection and display system.

FIG. 13 depicts a schematic of an exemplary embodiment of a system with leg and arm motion sensors 52 connected directly (hard wired) to the chest protector hub 53. This is a similar configuration as FIG. 4 except there are no transmitters as per FIG. 4.

Figure 14:
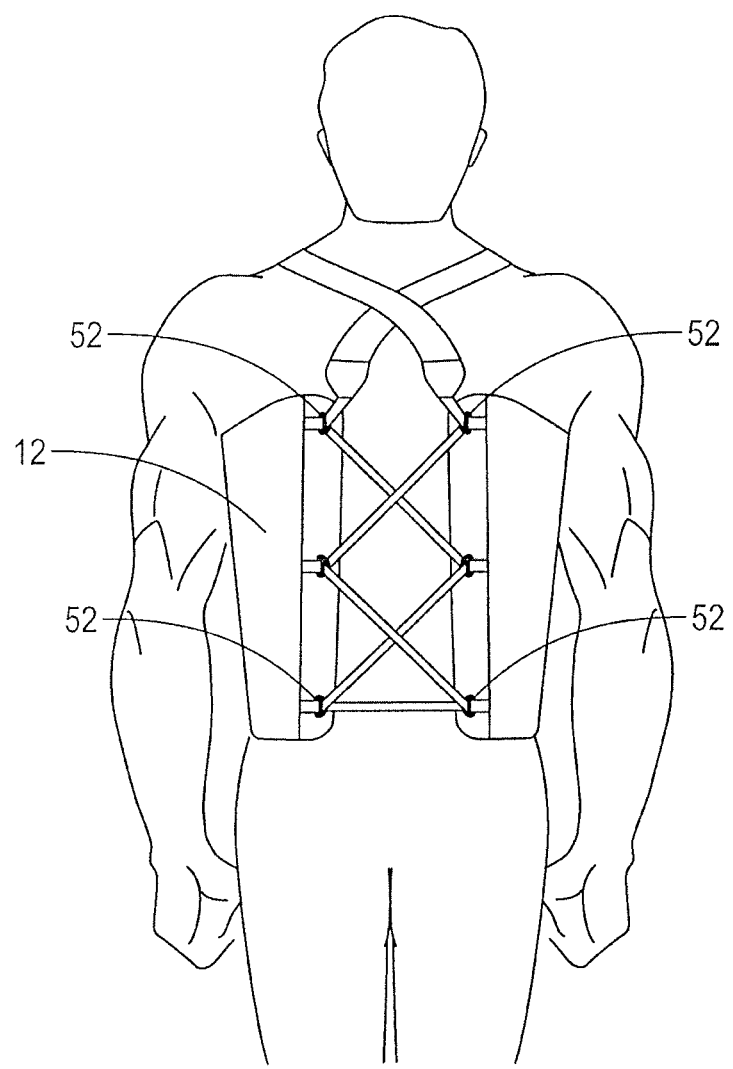
FIG. 14 depicts leg and arm motion sensors on the trunk protector.

FIG. 14 depicts exemplary locations of the leg and arm motion sensors 52 on the chest protector 12.

Figure 15:
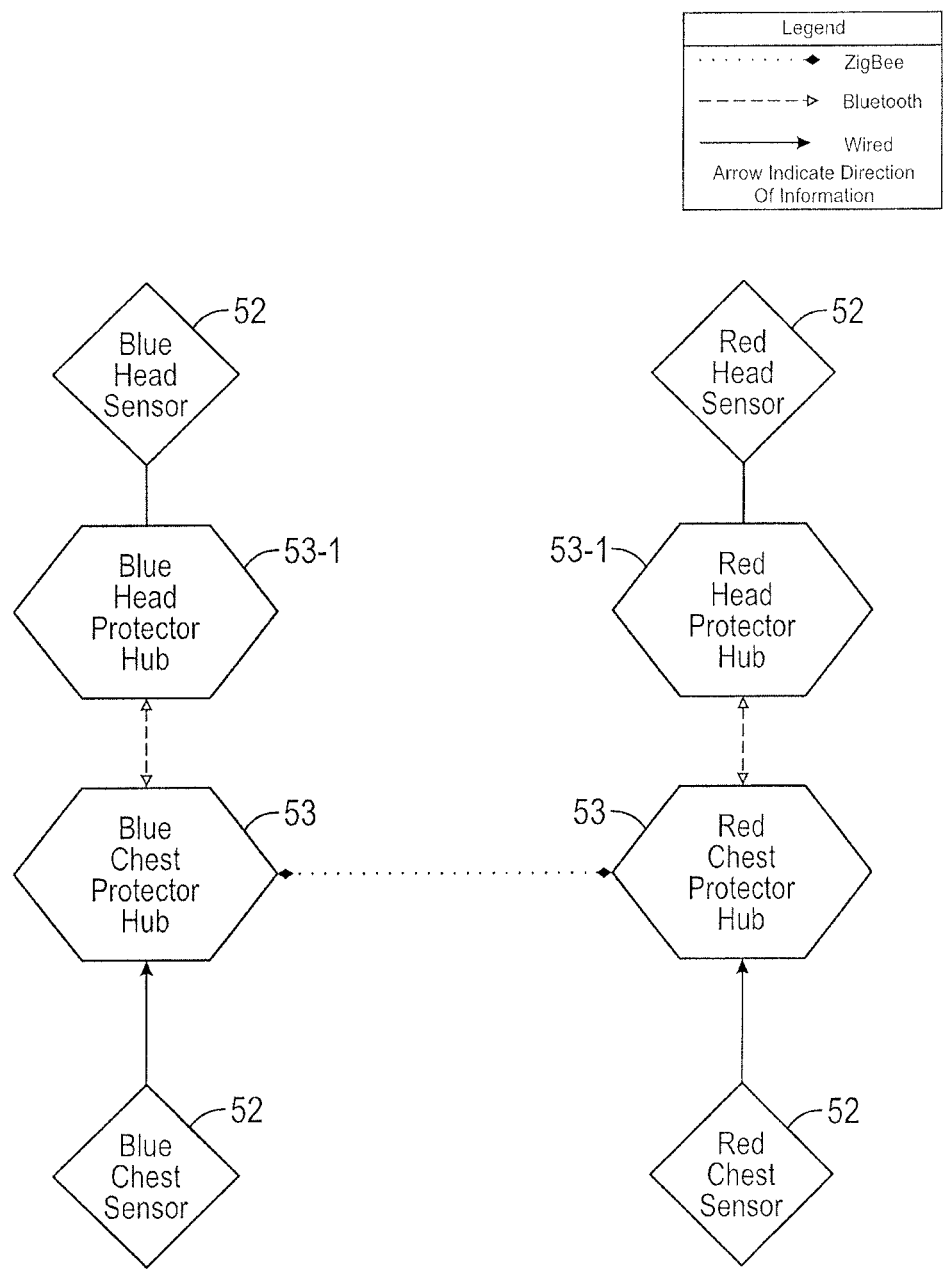
FIG. 15 depicts a recreational version of an exemplary embodiment the system with only a trunk and head protector.

FIG. 15 depicts a schematic of a recreational version of the system wherein there is only a pair of chest protectors and head protectors, with the blue and red chest protector hubs 53 in communication with each other. In an alternative exemplary embodiment, the recreational version does not include head protectors.

Figure 16A:
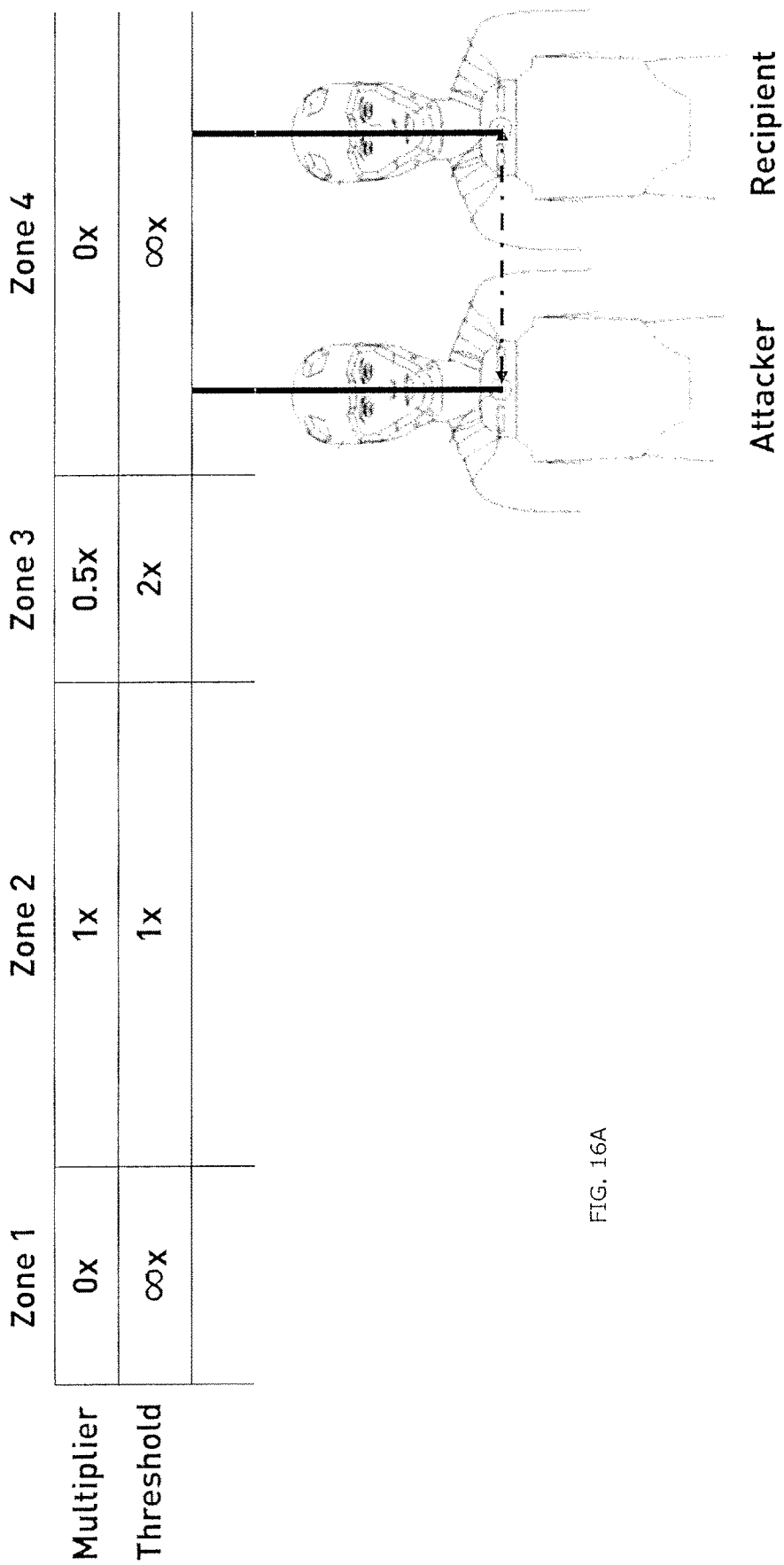
FIGS. 16A and 16B depict the distance-sensing component of the data collection and display system.
Figure 16B:
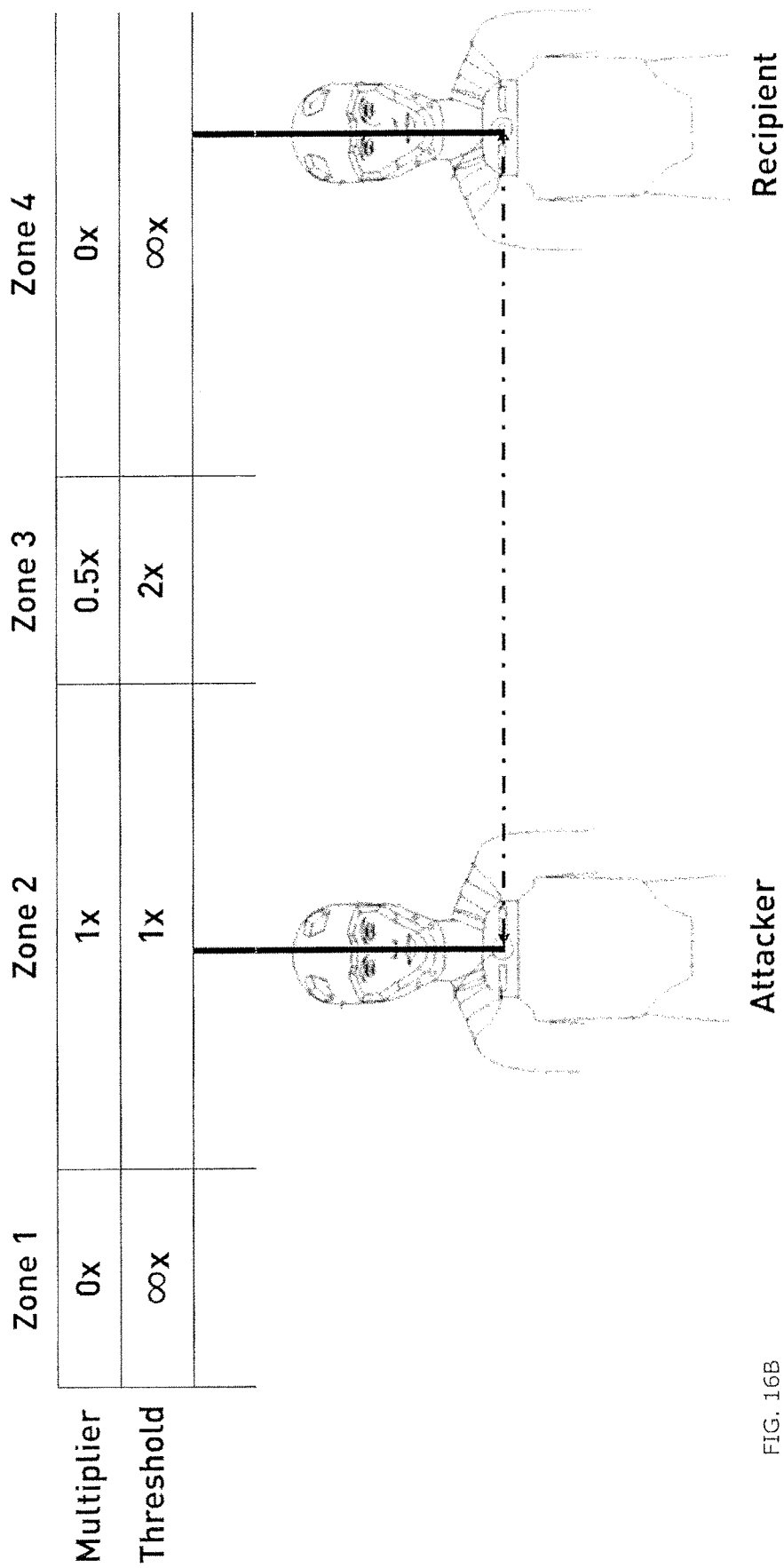

Referring now to FIGS. 16A and 16B, there is depicted two scenarios wherein contestants are too close in distance from each other (Zone 4) for a score to register (FIG. 16A) and wherein contestants are at an acceptable distance from each other (Zone 2) for a score to register.

FIG. 16A depicts a scenario in which the attacking contestant is within the range of Zone 4 relative to the contestant receiving the hit. In this example, Zone 4 could apply a 0 coefficient to the hit score (called a multiplier), and/or multiply the set minimum threshold for an attack to score by an infinite amount, both of which would effectively nullify the attack.

FIG. 16B depicts a scenario in which the attacking contestant is within the range of Zone 2 relative to the contestant receiving the hit. In this example, Zone 2 could apply a 1 coefficient to the hit score (called a multiplier), and/or multiply the set minimum threshold for an attack to score by 1, both of which would effectively offer no modification to the score of the action.

Both FIGS. 16A and 16B depict 4 zones (Zone 1, Zone 2, Zone 3 and Zone 4) which are set to assign a value to a strike depending on the Zone the attacker is in, in relation to the recipient.

The following is an example of the manufacture of an exemplary embodiment of the system described herein.

Step 1. Source a vinyl that is waterproof (and ideally bacteria proof) that can take many impacts from kicks and punches (i.e. marine grade vinyl is a good choice) and cut it into the shape of a chest protector known to persons of ordinary skill in the art.

Step 2. Cut one pattern for the front side of the chest protector and another for the back side of the chest protector.

Step 3. Join (or assemble in any fashion, such as by sewing or stitching), along the periphery, the front and back sides of the chest protector.

Step 4. Make an incision proximate the middle of the back side of the chest protector to allow for the insertion of at least one impact sensor, protective padding, a power source (such as a battery) and electronics board as required for data collection and processing and for the visual display of player health and timer. The incision may then be sealed with an enclosure system such as a zipper or a Velcro™ type fastener to allow access the interior of the chest protector and the components therein.

The sensor may be one of many options as described herein, however the minimum characteristic is the sensor should be able to:
1. detect an impact on the chest protector, preferably "trembling shock", more preferably between the range of from about 50 N of force to about 9000 N of force;
2. communicate the force of an impact on the sensor to a hub or processor;
3. be worn on a person; and
4. be durable (for example take up to 600,000 impacts of up to 9000 N of force per impact).

The protective padding may be one of many options know to persons of ordinary skill in the art. It is advantageous to use a light weight padding (such as <3 lbs) that is comfortable to the wearer and can be worn around a person and absorb impacts from kicks and punches.

Step 5. Create a custom electronics board with the following characteristics:
1. able to connect to the sensor and read its signal from impacts;
2. be enclosed in a housing able to withstand any impact common in combat sports, one example being of a minimum 9000 N force;
3. able to display information on the chest protector the status of a match (including each player's health) as well as the time left in the match;
4. a physical control panel where a user may change the settings of a match (match length time, game mode, health sensitivity) right on the device. The control panel may also have the ability to show the status of other parts of a match (sync status to other devices);
5. a radio communication device for communication of status and data to other devices (i.e. another chest protector, a phone or a computer); and
6. an area to insert a charger for charging the power source (such as a rechargeable battery or batteries).

Step 6. Load the software into the electronics board that provides the communication protocols to various devices and the different game modes available.

In one embodiment, Step 5 further comprises a transmitter, preferably a transmitter and receiver for measuring distance between at least two signal sources. In an alternative embodiment, said transmitter is integral with said radio communication device.

The following provides further advantages of one embodiment of the system described herein versus prior art systems.

The Present System utilizes a thick (in one embodiment ≈0.5") triboelectric foam sensor to sense impacts on the body protector. Such type of sensor makes use of the microscale-friction of conductive fibers against a polyurethane matrix during a straining event to produce a momentary electrostatic charge in a single electrode. This effect is proportional to power/energy absorbed by the sensor, a much truer and more meaningful measure of impact intensity according to academic bio-medical studies. The triboelectric sensor foam also functions as protection for itself and the wearer, the triboelectric foam is volumetric and an extremely uniform, location-independent sensor, and the combination sensing/protective foam is less costly to manufacture and less complex to operate than prior art systems.

The Present System head protector is composed of the same type of sensor foam as in the Present System body protector, but using a thicker (in one embodiment lighter foam for better cranial protection. Using a unified sensor/protective element allows more sensor coverage (minimizes phantom contacts and able to determine the strength of an impact on a combatant using the present system) than the prior art as well as being less costly to manufacture and less complex to operate.

The "hit validation" system of the Present System model is based on motion sensors (including accelerometers) which sense the movements of the striker to identify with positive certainty not only the legality, but also the type of technique. Also rendered is the speed of each strike and other mechanical statistics. This acceleration-based method is also more simple and modular, only requiring additional hardware on the striker, independent of the equipment worn by the impacted player.

The Present System is built around an energy-based scoring scheme similar to that of fighting video games in which players are allotted a quantity of "health" or energy at the beginning of each round which is depleted by attacks from the opposite player. Energy is depleted by each successful attack, non-discretely proportional to impact intensity. The player to deplete his opponent's energy first, or has more energy remaining at the end of a round is declared the winner of the round. The deductive nature of this energy scoring limits the danger of excessive beating a player may experience, and is more intuitively understandable. The Present System hit validation sensors are capable of automatically characterizing techniques, and scoring value is inherently independent of technique, reducing, preferably eliminating the need for judges and trigger boxes.

Extensive signal processing is incorporated in the Present System, in one embodiment with the triboelectric sensor. The Present System body protectors and head protectors are able to share in a mesh network with a control computer. This enables the body protectors and head protectors to keep score independently and in synchronization; enables combatants to engage in a combat sport without a control computer, and increases network stability. The score and clock are also displayed on the equipment worn by each combatant to alleviate the need to look away from one's opponent.

What has been described and illustrated herein are exemplary embodiments with many variations. The terms, descriptions and figures used herein are set forth by way of illustration only and are not meant as limitations. Those skilled in the art will recognize that many variations are possible within the spirit and scope of the disclosed subject matter in which all terms are meant in their broadest, reasonable sense unless otherwise indicated. Any headings utilized within the description are for convenience only and have no legal or limiting effect.

As many changes can be made to the exemplary embodiments without departing from the scope thereof; it is intended that all matter contained herein be considered illustrative and not in a limiting sense.

The invention claimed is:

1. A method of calculating a final value ($M_s$) of a scoring action using a data collection and display system in a combat sport wherein said final value is based on at least one of impact intensity and energy associated with a strike delivered by a combatant in a combat match or game mode between at least two opponents (or combatants), said method comprising:
   i) providing a trunk protector that is worn by the combatants and wherein said protector comprises at least one impact and/or energy sensor and at least one microprocessor, said microprocessor collecting and analyzing data from said at least one impact and/or energy sensor and using determined scoring actions corresponding to combatant actions, said trunk protector further comprising a display connected to said processor for displaying information selected from the group consisting of data collected and analyzed by said microprocessor, combatant status, combatant score, combatant health, match time, match number and combination thereof;
   ii) said microprocessor determining an individual raw magnitude of every scoring action $m_i$;

iii) said microprocessor assigning a placement value, determined by a scoring impact zone 1 on the combatants, to a $P_{l_i}$ constant;
iv) said microprocessor assigning an independent combination bonus multiplier value to $C_1$ constant;
v) said microprocessor assigning a magnitude, inclusive or exclusive of any modifying variable, per preference, of any desired scoring action to $A_1$ constant;
vi) said microprocessor assigning a magnitude, inclusive or exclusive of any modifying variable, per preference, of any desired scoring action to $A_2$ constant;
vii) said microprocessor assigning a time-dependent combination bonus modifier to $C_2$ constant;
viii) said microprocessor determining the amount of time elapsed between any scoring action and a previous scoring action $t_i$;
ix) said microprocessor assigning a value, of a threshold of elapsed time between scoring actions eligible for application of combination scoring augmentation, to $T_n$ constant; and
x) said microprocessor evaluating for $M_s$ and attributing to the relevant combatant to affect status of the match or game mode by using the following relationship:

$$M_s = m_i P_{l_i} + C_{1_n}\left(\frac{A_1 + A_2}{2}\right)\left(C_{2_n} - \frac{t_i}{T_n}\right)\Big| 0 < t_i \leq T_n.$$

2. The method of claim 1 wherein the placement modifier ($P_{l_i}$) coefficient is selected from a value of 1 for a legal body impact and 2 for a legal head impact.

3. A method of calculating a final value ($M_s$) of a scoring action using a data collection and display system in a combat sport wherein said final value is based on at least one of impact intensity and energy associated with a strike delivered by a combatant in a combat match or game mode between at least two opponents (or combatants), said method comprising:
i) providing a trunk protector that is worn by the combatants and wherein said protector comprises at least one impact and/or energy sensor and at least one microprocessor, said microprocessor collecting and analyzing data from said at least one impact and/or energy sensor and using determined scoring actions corresponding to combatant actions, said trunk protector further comprising a display connected to said processor for displaying information selected from the group consisting of data collected and analyzed by said microprocessor, combatant status, combatant score, combatant health, match time, match number and combination thereof;
ii) said microprocessor determining an individual raw magnitude of every scoring action $m_i$;
iii) said microprocessor assigning a distance value, determined by the distance from the opponent at which a scoring attack was executed, to a $D_{z_i}$ constant;
iv) said microprocessor assigning a placement value, determined by a scoring impact zone 1 on the combatants, to a $P_{l_i}$ constant;
v) said microprocessor assigning an independent combination bonus multiplier value to $C_1$ constant;
vi) said microprocessor assigning a magnitude, inclusive or exclusive of any modifying variable, per preference, of any desired scoring action to $A_1$ constant;
vii) said microprocessor assigning a magnitude, inclusive or exclusive of any modifying variable, per preference, of any desired scoring action to $A_2$ constant;
viii) said microprocessor assigning a time-dependent combination bonus modifier to $C_2$ constant;
ix) said microprocessor determining the amount of time elapsed between any scoring action and a previous scoring action $t_i$;
x) said microprocessor assigning a value, of a threshold of elapsed time between scoring actions eligible for application of combination scoring augmentation, to $T_n$ constant; and
xi) said microprocessor evaluating for $M_s$ and attributing to the relevant combatant to affect status of the match or game mode by using the following relationship:

$$M_s = D_{z_i} m_i P_{l_i} + C_{1_n}\left(\frac{D_z A_1 + D_z A_2}{2}\right)\left(C_{2_n} - \frac{t_i}{T_n}\right)\Big| 0 < t_i \leq T_n.$$

4. A data collection and display system for use in a combat sport match for calculating a final value ($M_s$) of a scoring action based on at least one of impact intensity and energy associated with a strike delivered by a combatant in a combat match or a game mode between at least two opponents (or combatants), said system comprising:
a trunk protector for each combatants and wherein said trunk protector comprises:
at least one impact and/or energy sensor;
at least one microprocessor integral with said trunk protector, for collecting and analyzing data from said at least one impact and/or energy sensor to determine said final value of a scoring action, said at least one microprocessor using determined scoring actions corresponding to combatant actions to:
(i) determine an individual raw magnitude of every scoring action $m_i$;
(ii) assign a placement value, determined by a scoring impact zone 1 on the combatants, to a $P_{l_i}$ constant;
(iii) assign an independent combination bonus multiplier value to a $C_1$ constant;
(iv) assign a magnitude, inclusive or exclusive of any modifying variable, per preference, of any desired scoring action to an $A_1$ constant;
(v) assign a magnitude, inclusive or exclusive of any modifying variable, per preference, of any desired scoring action to an $A_2$ constant;
(vi) assign a time-dependent combination bonus modifier to a $C_2$ constant;
(vii) determine an amount of time elapsed between any scoring action and a previous scoring action $t_i$;
(viii) assign a value, of a threshold of elapsed time between scoring actions eligible for application of combination scoring augmentation, to a $T_n$ constant; and
(ix) evaluate $M_s$ and attributing to the relevant combatant to affect status of the match or the game mode by using the following relationship:

$$M_s = m_i P_{l_i} + C_{1_n}\left(\frac{A_1 + A_2}{2}\right)\left(C_{2_n} - \frac{t_i}{T_n}\right)\Big| 0 < t_i \leq T_n;$$

at least one display area, integral with said trunk protector, for displaying information selected from the group consisting of: data collected and analyzed by said at least one microprocessor, combatant status, combatant score, combatant health, match time, match number and combinations thereof; and at least one power source, integral with said trunk protector, for powering at least one of said at least one impact and/or energy sensor, said at least one microprocessor and said at least one display area.

5. The system of claim 4 wherein said placement modifier coefficient $P_{l_i}$ is selected from a value of 1 for a legal body impact and 2 for a legal head impact.

6. A data collection and display system for use in a combat sport match for calculating a final value ($M_s$) of a scoring action based on at least one of impact intensity and energy associated with a strike delivered by a combatant in a combat match or a game mode between at least two opponents (or combatants), said system comprising:

a trunk protector for each combatants and wherein said trunk protector comprises:

at least one impact and/or energy sensor;

at least one microprocessor integral with said trunk protector, for collecting and analyzing data from said at least one impact and/or energy sensor to determine said value of final value of a scoring action, said at least one microprocessor using determined scoring actions corresponding to combatant actions to:

(i) determine an individual raw magnitude of every scoring action $m_i$;

(ii) assign a distance value, determined by a distance from a combatant at which a scoring attack was executed, to a $D_{z_i}$ constant;

(iii) assign a placement value, determined by a scoring impact zone l on the combatants, to a $P_{l_i}$ constant;

(iv) assign an independent combination bonus multiplier value to a $C_1$ constant;

(v) assign a magnitude, inclusive or exclusive of any modifying variable, per preference, of any desired scoring action to an $A_1$ constant;

(vi) assign a magnitude, inclusive or exclusive of any modifying variable, per preference, of any desired scoring action to an $A_2$ constant;

(vii) assign a time-dependent combination bonus modifier to a $C_2$ constant;

(viii) determine an amount of time elapsed between any scoring action and a previous scoring action $t_i$;

(ix) assign a value, of a threshold of elapsed time between scoring actions eligible for application of combination scoring augmentation, to a $T_n$ constant; and (x) evaluate $M_s$ and attributing to the relevant combatant to affect status of the match or the game mode by using the following relationship:

$$M_s = D_{z_i} m_i P_{l_i} + C_{1_n} \left( \frac{D_z A_1 + D_z A_2}{2} \right) \left( C_{2_n} - \frac{t_i}{T_n} \right) \bigg| 0 < t_i \le T_n;$$

at least one display area, integral with said trunk protector, for displaying information selected from the group consisting of: data collected and analyzed by said at least one microprocessor, combatant status, combatant score, combatant health, match time, match number and combinations thereof; and at least one power source, integral with said trunk protector, for powering at least one of said at least one impact and/or energy sensor, said at least one microprocessor and said at least one display area.

* * * * *